United States Patent
Assaraf et al.

(10) Patent No.: US 8,630,703 B2
(45) Date of Patent: Jan. 14, 2014

(54) TREATMENT UTILIZING HYDROPHOBIC WEAK BASES CHEMOTHERAPEUTIC AGENTS AND ILLUMINATION

(75) Inventors: Yehuda G. Assaraf, Doar-Na Misgav (IL); Yamit Adar Turgeman, Haifa (IL); Andrzej M. Skladanowski, Gdansk (PL); Arjan W. Griffioen, Heemstede (NL); Henk Verheul, Amstelveen (NL); Kristy Gotink, Wichmond (NL); Hubert Van Den Bergh, Goumoens-la-Ville (CH); Patrycja Nowak-Sliwinska, St. Genis-Pouilly (FR)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/414,879

(22) Filed: Mar. 8, 2012

(65) Prior Publication Data

US 2012/0283620 A1    Nov. 8, 2012

Related U.S. Application Data

(60) Provisional application No. 61/450,688, filed on Mar. 9, 2011.

(51) Int. Cl.
*C07D 219/08* (2006.01)

(52) U.S. Cl.
USPC .......... 604/20; 546/103; 546/63; 546/66; 546/102; 514/21.1; 514/283; 514/288; 514/313; 514/287; 514/297

(58) Field of Classification Search
USPC .......... 604/20; 514/21.1, 283, 288, 313, 287, 514/297; 546/103, 102, 63, 66
See application file for complete search history.

(56) References Cited

U.S. PATENT DOCUMENTS

| | | |
|---|---|---|
| 6,573,293 B2 | 6/2003 | Tang et al. |
| 7,211,600 B2 | 5/2007 | Lipson et al. |
| 2010/0256136 A1 | 10/2010 | Pandey et al. |

OTHER PUBLICATIONS

Gotink et al. "Lysosomal Sequestration of Sunitinib: A Novel Mechanism of Drug Resistance", Clinical Cancer Research, 17(23): 7337-7346, Oct. 6, 2011.

Bram et al. "Structural Determinants of Imidazoacridinones Facilitating Antitumor Activity Are Crucial for Substrate Recognition by ABCG2", Molecular Pharmacology, 75(5): 1149-1159, 2009.

Dallabrida et al. "Damage, Repair, and Remodeling of the Heart: Sunitinib-Induced Cardiotoxicity Is Mediated in Part Via Direct Effects on Cardiac Myocytes and Smooth Muscle Cells", Circulation, 116(II_311): Abstract 1505, 2007.

Gao et al. "Mechanism of Action and Spectrum of Cell Types Susceptible to Doxorubicin Photochemotherapy", Cancer Chemotherapy and Pharmacology, 40(2): 138-142, 1997. Abstract.

(Continued)

*Primary Examiner* — Savitha Rao

(57) ABSTRACT

Hydrophobic weak base compounds such as hydrophobic weak base chemotherapeutic agents (which are not an anthracycline) for use in the treatment of medical conditions such as proliferative disease or disorder in a subject, in combination with illumination of a region in a body of the subject which is characterized by the presence of proliferating cells, are disclosed. The hydrophobic weak base compound and a wavelength of illumination are selected such that the hydrophobic weak base compound acts as a therapeutically effective photosensitizer when exposed to the illumination.

9 Claims, 29 Drawing Sheets
(23 of 29 Drawing Sheet(s) Filed in Color)

(56) References Cited

OTHER PUBLICATIONS

Hsu et al. "Enhanced Cytotoxicity of Doxorubicin by Micellar Photosensitizer-Mediated Photochemical Internalization in Drug-Resistant MCF-7 Cells", 13th International Conference in Biomedical Engineering, IFMBE Proceedings, 23(Track 4): 1451-1454, 2009. Abstract.

Kirveliene et al. "Schedule-Dependent Interaction Between Doxorubicin and mTHPC-Mediated Photodynamic Therapy in Murine Hepatoma In Vitro and In Vivo", Cancer Chemotherapy and Pharmacology, 57(1): 65-72, Jan. 2006. Abstract.

Koceva-Chyla et al. "Combined Effect of Low-Power Laser Irradiation and Anthraquinone Anticancer Drug Aclarubicin on Survival of Immortalized Cells: Comparison With Mitoxantrone", Cell Biology International, 30: 645-652, 2006.

Lanks et al. "Photodynamic Enhancement of Dororubicin Cytotoxicity", Cancer Chemotherapy and Pharmacology, 35(1): 17-20, 1994. Abstract.

Li et al. "Spectroscopic Studies of Cutaneous Photosensitizing Agents—X. A Spin-Trapping and Direct Electron Spin Resonance Study of the Photochemical Pathways of Daunomycin and Adriamycin", Photochemistry and Photobiology, 45(5): 565-570, May 1987. Abstract.

Lou et al. "Reversal of Doxorubicin Resistance in Breast Cancer Cells by Photochemical Internalization", International Journal of Cancer, 119: 2692-2698, 2006.

Quiogue et al. "Signaling From Lyosomes Enhances Mitochondria-Mediated Photodynamic Therapy in Cancer Cells", Proceedings—Society of Photo-Optical Instrumentation Engineers, 7380(73800c): 1-8, Jul. 12, 2009.

Sharman et al. "Targeted Photodynamic Therapy Via Receptor Mediated Delivery Systems", Advanced Drug Delivery Reviews, 56: 53-76, 2004.

| Compound | R1 | R2 | R3 | R6 | R14 | R$_{a,b}$ | n |
|---|---|---|---|---|---|---|---|
| C-1330 | OMe | H | H | H | H | Et | 2 |
| C-1375 | OMe | H | H | H | Me | Me | 3 |
| C-1379 | OMe | H | H | H | Me | Et | 3 |
| C-1311 | OH | H | H | H | H | Me | 3 |

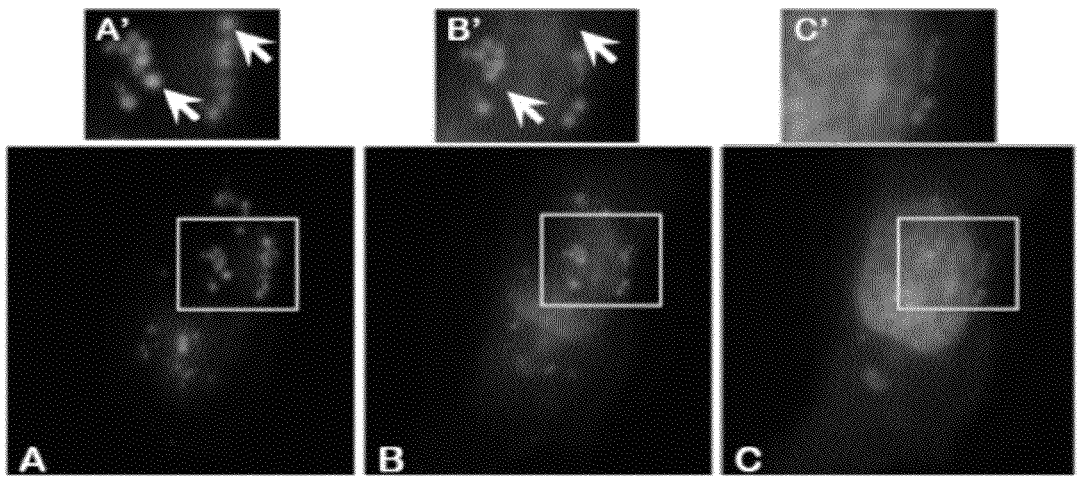
FIG. 6A          FIG. 6B          FIG. 6C
FIG. 6D          FIG. 6E          FIG. 6F
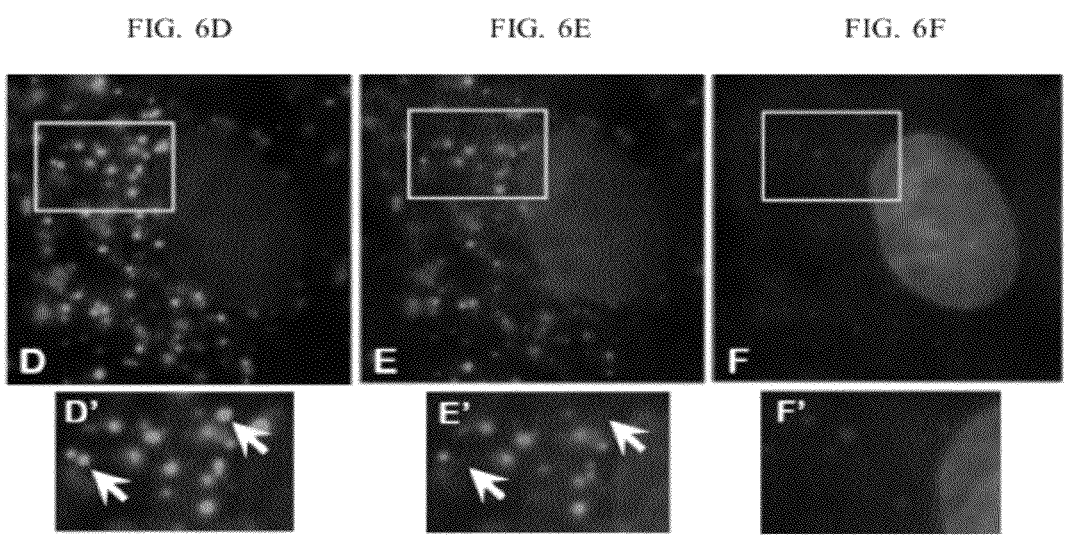

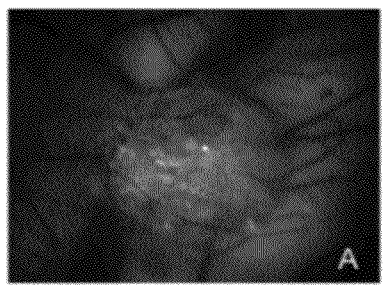 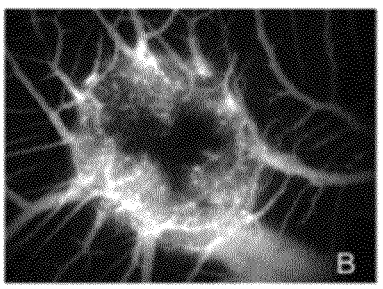 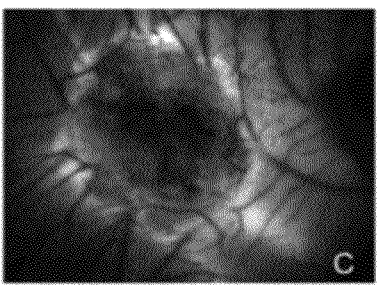
FIG. 28A  FIG. 28B  FIG. 28C
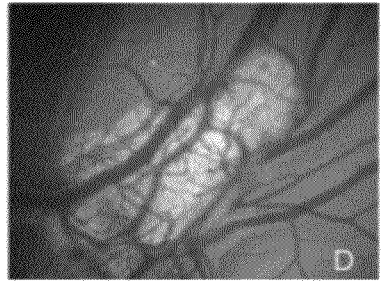 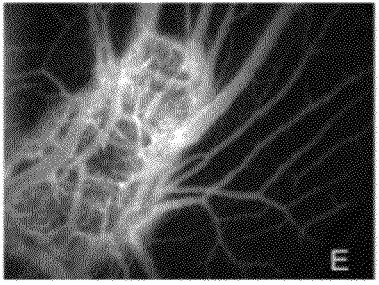 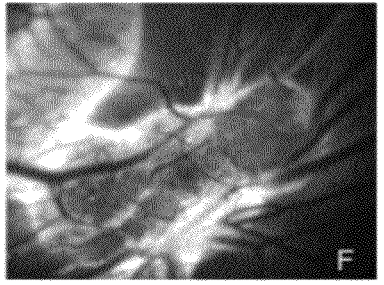
FIG. 28D  FIG. 28E  FIG. 28F FIG. 29A
FIG. 29B
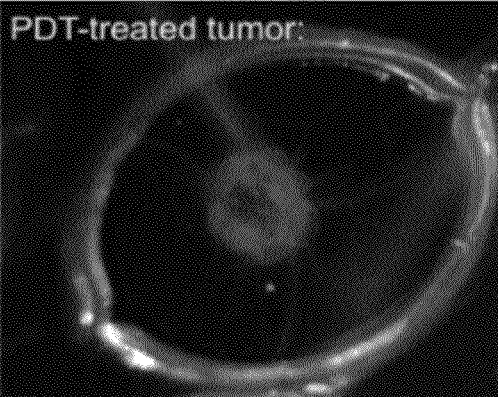 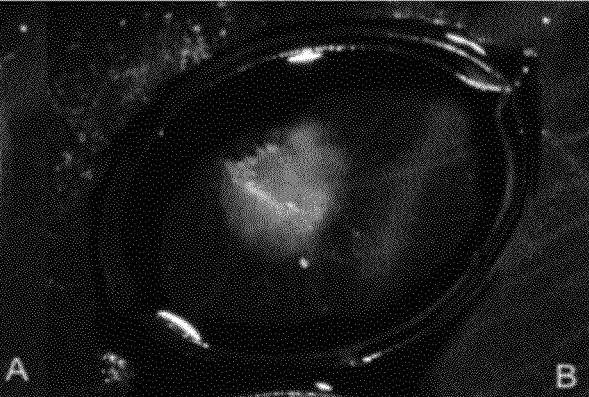
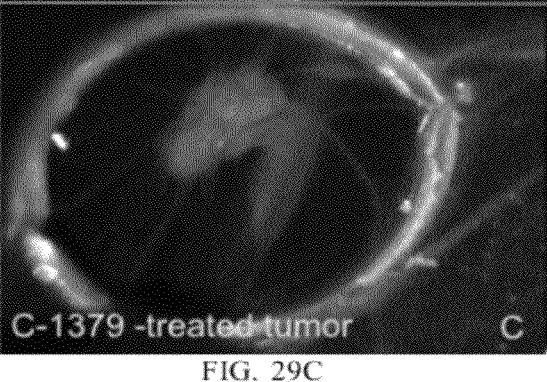 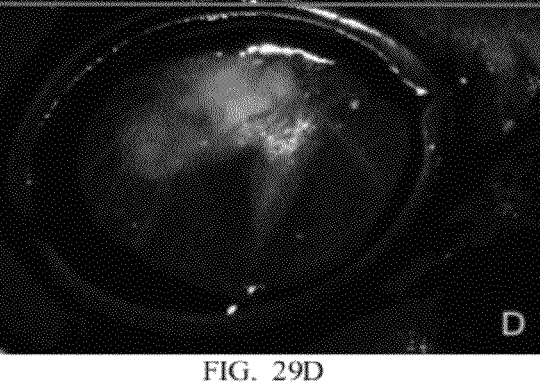
FIG. 29C
FIG. 29D

TREATMENT UTILIZING HYDROPHOBIC WEAK BASES CHEMOTHERAPEUTIC AGENTS AND ILLUMINATION

RELATED APPLICATION

This application claims the benefit of priority under 35 USC 119(e) of U.S. Provisional Patent Application No. 61/450,688 filed Mar. 9, 2011, the contents of which are incorporated herein by reference in their entirety.

FIELD AND BACKGROUND OF THE INVENTION

The present invention, in some embodiments thereof, relates to therapy and, more particularly, but not exclusively, to novel methodologies for treating medical conditions such as proliferative diseases and disorders, and drug resistant as well as multidrug resistant (MDR) conditions in particular.

Cancer is a major cause of mortality worldwide. Despite advancements in diagnosis and treatment, there remains a great need for novel methods of treating cancer and for identifying novel agents and approaches for overcoming proliferation of cancer cells, particularly drug resistant cancer cells.

Multidrug resistance (MDR) towards chemotherapeutic agents poses a major impediment towards curative chemotherapy of various human malignancies. In this respect, MDR is an extensively studied mechanism of anticancer drug resistance. MDR is mediated by members of the ATP-binding cassette superfamily of transporters including ABCB1 (P-glycoprotein), ABCC1 (MRP1) and ABCG2 (BCRP). Recognizing a plethora of hydrophobic, hydrophilic and amphiphilic cytotoxic substrates, these ATP-driven efflux pumps extrude structurally distinct endobiotics and xenobiotics out of malignant tumors, many of which are key antitumor agents, thereby resulting in a wide spectrum of drug resistance.

Imidazoacridinones (IAs) are a class of planar imidazoacridinone-based cytotoxic fluorochromes which exhibited significant clinical activity against colorectal and breast cancer [Skladanowski et al. *Mol Pharmacol* 1996, 49:772-780]. IAs are weak bases which are hydrophobic in a non-protonated state, but more water-soluble in a protonated, positively charged state. The structure of the exemplary IAs C-1330, C-1375, C-1379 and C-1311 is shown in FIG. 1, and includes an imidazole ring, as well as an amine group (depicted as "NRa,b" in FIG. 1), both of which comprise a weakly basic nitrogen atom which may become protonated, and therefore positively charged, under physiological conditions in acidic organelles such as lysosomes and endosomes.

IAs are somewhat similar in structure to acridine orange, an established fluorophore that is known to concentrate within lysosomes in viable cells. Acridine orange also binds to DNA, a phenomenon which is utilized for staining DNA. Other acridine-based compounds, including IAs, have also been shown to bind to DNA [Dziegielewski et al., *Biochem Pharmacol* 2002, 63:1653-1662; Bram et al., *Mol Pharmacol* 2009, 75:1149-1159]. However, DNA binding by IAs does not appear to contribute significantly to the cytotoxic activity of IAs [Dziegielewski et al., *Biochem Pharmacol* 2002, 63:1653-1662]. Instead, the cytotoxic activity of IAs appears to be primarily a result of topoisomerase II inhibition [Skladanowski et al. *Mol Pharmacol* 1996, 49:772-780]. U.S. Patent Application No. 20100137351 and Bram et al. [*Mol Pharmacol* 2009, 75:1149-1159] describe IA compounds characterized by anti-cancer activity, some of which are extruded out of MDR cells via the MDR efflux pump ABCG2.

In general, IA compounds lacking a hydroxyl group at one of the $R_1$-$R_3$ positions shown in FIG. 1 and/or with a longer distal aliphatic side chain ($NH(CH_2)nNRa,b$ in FIG. 1) were not recognized as transport substrates by ABCG2 and hence overcame the MDR displayed by ABCG2-overexpressing cells.

Sunitinib is a member of a family of pyrrole substituted 2-indolinone compounds, reported as being receptor tyrosine kinase inhibitors (see, U.S. Pat. Nos. 6,573,293 and 7,211,600). Sunitinib inhibits cellular signaling via a variety of receptors which play a role in tumor angiogenesis and tumor cell proliferation. Hence, the simultaneous inhibition of these receptors promotes reduced tumor vascularization (i.e. exhibits an anti-angiogenic effect) and cancer cell death. However, the diversity of receptors targeted by sunitinib results in many side effects, such as hand-foot syndrome, stomatitis and other dermatological toxicities.

Photodynamic therapy (PDT) is a medical technique wherein a photosensitizer applied to a subject is excited by illumination from an external light source. The excited photosensitizer may produce reactive oxygen species (ROS) capable of killing cells and/or closing/opening blood vessels. The history, mechanism of action and applications of PDT have been reviewed, for example, by van den Bergh and Ballini [in *Lasers in Ophthalmology—Basic, Diagnostic and Surgical Aspects*, edited by Fankhauser and Kwasniewska, 2003, Kugler Publications, The Hague] and Sharman et al. [*Adv Drug Delivery Rev* (2004) 56:53-76].

A photosensitizer is generally selected to be relatively non-toxic in the absence of light, such that directing illumination to a particular site provides a localized phototoxicity. Photosensitizers used for PDT are typically porphyrins and structurally-related compounds such as chlorins, texaphyrins and phthalocyanines, or porphyrin precursors such as aminolevulinic acid. Rhodamine dyes have also been used for PDT [Haghighat et al., *Laryngoscope* (1992) 102:81-87].

It has been reported that photosensitizers differentially target certain intracellular organelles such as mitochondria, endoplasmic reticulum or lysosomes, and that a photosensitizer which targets lysosomes causes release of proteolytic lysosomal enzyme [Quiogue et al., *Proc Soc Photo Opt Instrum Eng* (2009) 7380:1-8]. However, mitochondria are more often considered as an effective target for photosensitizers [Quiogue et al., *Proc Soc Photo Opt Instrum Eng* (2009) 7380:1-8].

The combination of administration of chemotherapeutic agents and PDT with a photosensitizer has been studied. U.S. Patent Application No. 20100256136 describes a method of enhancing PDT efficacy in tissue which expresses ABCG2 by introducing a tyrosine kinase inhibitor prior to PDT. The tyrosine kinase inhibitor is introduced in order to inhibit efflux of the PDT photosensitizer.

Phthalocyanine-based PDT has been used in combination with doxorubicin in order to overcome doxorubicin resistance mediated by accumulation of doxorubicin in cellular organelles. It has been reported that the PDT disrupts endosomal/lysosomal membranes in order to release the doxorubicin from organelles to the nuclei, where doxorubicin exerts a cytotoxic effect [Hsu et al., *IFMBE Proceedings* (2009) 23:1451-1454].

PDT was reported to potentiate the efficacy of doxorubicin, and vice versa, with the combination being most effective when doxorubicin was administered immediately after light exposure [Kirveliene et al., *Cancer Chemother Pharmacol* (2006) 57:65-72]. PDT followed by administration of doxorubicin has been suggested as a technique for overcoming MDR in cancer cells [Lou et al., *Int J Cancer* (2006) 119:

2692-2698]. In several studies, it has been reported that the cytotoxicity of doxorubicin, an anthracycline drug which targets topoisomerase II and intercalates into DNA, can be enhanced by laser irradiation [Lanks et al., *Cancer Chemother Pharmacol* (1994) 35:17-20; Gao et al., *Cancer Chemother Pharmacol* (1997) 40:138-42]. Some anthracyclines have been proposed as potential photosensitizers for PDT [Koceva-Chyla et al., *Cell Biol Int* (2006) 30:645-652; Li and Chignell, *Photochem Photobiol* (1987) 45:565-570].

Additional background art includes Koceva-Chyla et al. [*Cell Biol Int* (2006) 30:645-652] and Dallbrida et al. [*Circulation* (2007) 116:II 311] and Gotink et al. *Clin Cancer Res.* 2011; 17(23):7337-46.

SUMMARY OF THE INVENTION

The present inventors have now surprisingly uncovered that chromophoric, hydrophobic weak bases can be efficiently used as photosensitizers when administered to a subject in combination with illumination, and can thus be efficiently utilized in PDT, particularly for treating MDR cancer.

The present inventors have demonstrated that hydrophobic weak base chemotherapeutic agents efficiently accumulate within lysosomes, and that illumination of cells loaded with such agents who are further chromophoric resulted in rupture of lysosomes and cell death.

The present inventors have also demonstrated that MDR cells possess a larger number of lysosomes than drug sensitive (non-MDR) cells. Consequently, lysosomal photodestruction resulted in markedly lower $IC_{50}$ values of such chemotherapeutic agents in illuminated MDR cells, compared to non-illuminated cells.

The present inventors have also demonstrated that illumination following in vivo administration of chromophoric and hydrophobic weak base compounds, such as imidazoacridinones and sunitinib, leads to angio-occlusion, resulting in efficient destruction of vasculature. As further demonstrated by the inventors, this application can be used to destroy tumor vasculature and to inhibit tumor growth.

According to an aspect of some embodiments of the present invention, there is provided a method of treating a proliferative disease or disorder in a subject in need thereof, the method comprising administering to the subject a chemotherapeutic agent and illuminating a region in a body of the subject which is characterized by the presence of proliferating cells, wherein the chemotherapeutic agent is a hydrophobic weak base, and wherein the chemotherapeutic agent and a wavelength of the illumination are selected such that the chemotherapeutic agent acts as a therapeutically effective photosensitizer when exposed to the illumination, with the proviso that the chemotherapeutic agent is not an anthracycline. Thus, the chemotherapeutic agent is photosensitive with respect to at least some wavelengths.

According to an aspect of some embodiments of the present invention, there is provided a hydrophobic weak base chemotherapeutic agent for use in the treatment of a proliferative disease or disorder in a subject in need thereof in combination with illumination of a region in a body of the subject which is characterized by the presence of proliferating cells, wherein the chemotherapeutic agent and a wavelength of the illumination are selected such that the chemotherapeutic agent acts as a therapeutically effective photosensitizer when exposed to the illumination, with the proviso that the chemotherapeutic agent is not an anthracycline.

According to an aspect of some embodiments of the present invention, there is provided a use of a hydrophobic weak base chemotherapeutic agent in the manufacture of a medicament for the treatment of a proliferative disease or disorder in a subject in need thereof, the medicament being identified for use in combination with illumination of a region in a body of the subject which is characterized by the presence of proliferating cells, wherein the chemotherapeutic agent and a wavelength of the illumination are selected such that the chemotherapeutic agent acts as a therapeutically effective photosensitizer when exposed to the illumination, with the proviso that the chemotherapeutic agent is not an anthracycline.

According to an aspect of some embodiments of the present invention, there is provided a method of treating a proliferative disease or disorder in a subject in need thereof, the method comprising administering to the subject an imidazoacridinone chemotherapeutic agent and illuminating a region in a body of the subject which is characterized by the presence of proliferating cells, wherein the imidazoacridinone chemotherapeutic agent is a hydrophobic weak base, and wherein the imidazoacridinone chemotherapeutic agent and a wavelength of the illumination are selected such that the chemotherapeutic agent acts as a therapeutically effective photosensitizer when exposed to the illumination.

According to an aspect of some embodiments of the present invention, there is provided an imidazoacridinone chemotherapeutic agent, for use in the treatment of a proliferative disease or disorder in a subject in need thereof in combination with illumination of a region in a body of the subject which is characterized by the presence of proliferating cells, wherein the imidazoacridinone chemotherapeutic agent is a hydrophobic weak base, and wherein the imidazoacridinone chemotherapeutic agent and a wavelength of the illumination are selected such that the chemotherapeutic agent acts as a therapeutically effective photosensitizer when exposed to the illumination.

According to an aspect of some embodiments of the present invention, there is provided a use of an imidazoacridinone chemotherapeutic agent in the manufacture of a medicament for the treatment of a proliferative disease or disorder in a subject in need thereof, the medicament being identified for use in combination with illumination of a region in a body of the subject which is characterized by the presence of proliferating cells, wherein the imidazoacridinone chemotherapeutic agent is a hydrophobic weak base, and wherein the imidazoacridinone chemotherapeutic agent and a wavelength of the illumination are selected such that the chemotherapeutic agent acts as a therapeutically effective photosensitizer when exposed to the illumination.

According to an aspect of some embodiments of the present invention, there is provided a method of treating a proliferative disease or disorder in a subject in need thereof, the method comprising administering to the subject a chemotherapeutic agent which is a receptor tyrosine kinase inhibitor and illuminating a region in a body of the subject which is characterized by the presence of proliferating cells, wherein the chemotherapeutic agent is a hydrophobic weak base, and wherein the chemotherapeutic agent and a wavelength of the illumination are selected such that the chemotherapeutic agent acts as a therapeutically effective photosensitizer when exposed to the illumination.

According to an aspect of some embodiments of the present invention, there is provided a chemotherapeutic agent which is a receptor tyrosine kinase inhibitor for use in the treatment of a proliferative disease or disorder in a subject in need thereof in combination with illumination of a region in a body of the subject which is characterized by the presence of proliferating cells, wherein the receptor tyrosine kinase inhibitor is a hydrophobic weak base, and wherein the receptor tyrosine kinase inhibitor and a wavelength of the illumination are selected such that the receptor tyrosine kinase inhibitor acts as a therapeutically effective photosensitizer when exposed to the illumination.

According to an aspect of some embodiments of the present invention, there is provided a use of a receptor tyrosine kinase inhibitor for the manufacture of a medicament for the treatment of a proliferative disease or disorder in a subject in need thereof, the medicament being identified for use in combination with illumination of a region in a body of the subject which is characterized by the presence of proliferating cells, wherein the receptor tyrosine kinase inhibitor is a hydrophobic weak base, and wherein the receptor tyrosine kinase inhibitor and a wavelength of the illumination are selected such that the receptor tyrosine kinase inhibitor acts as a therapeutically effective photosensitizer when exposed to the illumination.

According to an aspect of some embodiments of the present invention, there is provided a pharmaceutical composition comprising a therapeutically effective amount of a chemotherapeutic agent described herein in combination with chloroquine, and a pharmaceutically acceptable carrier.

According to some embodiments of the invention, the chemotherapeutic agent and the illumination are characterized in that an $IC_{50}$ value of the chemotherapeutic agent when exposed to the illumination is 10% or less of an $IC_{50}$ value of the chemotherapeutic agent in the absence of illumination, the $IC_{50}$ values being determined by an XTT cell viability assay.

According to some embodiments of the invention, the chemotherapeutic agent is selected from the group consisting of an imidazoacridinone, a receptor tyrosine kinase inhibitor, an actinomycin, a camptothecin, and an anthracenedione.

According to some embodiments of the invention, the imidazoacridinone has the general formula:

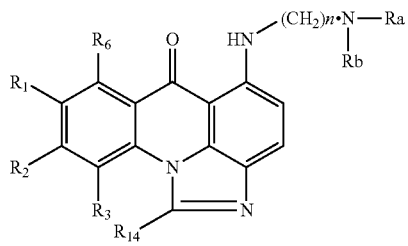

wherein:

$R_1$, $R_2$, $R_3$, $R_6$ and $R_{14}$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl;

Ra and Rb are each independently selected from the group consisting of hydrogen, alkyl, alkenyl, alkynyl, cycloalkyl, heteroalicyclic, aryl, and heteroaryl; and n is from 1 to 30.

According to some embodiments of the invention, $R_1$ is selected from the group consisting of hydroxy and alkoxy.

According to some embodiments of the invention, n is 2 or 3.

According to some embodiments of the invention, Ra and Rb are alkyl.

According to some embodiments of the invention, $R_{14}$ is selected from the group consisting of hydrogen and alkyl.

According to some embodiments of the invention, $R_2$, $R_3$ and $R_6$ are each hydrogen.

According to some embodiments of the invention, the receptor tyrosine kinase inhibitor has the general formula:

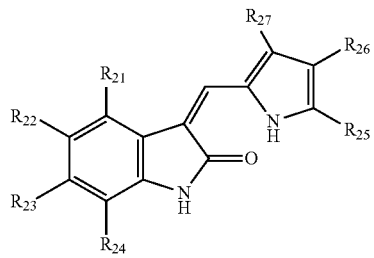

wherein:

$R_{21}$-$R_{27}$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl.

According to some embodiments of the invention, $R_{26}$ is —C(=O)NH—$R_{28}$, wherein $R_{28}$ is an amino-substituted alkyl.

According to some embodiments of the invention, the receptor tyrosine kinase inhibitor is selected from the group consisting of sunitinib and toceranib.

According to some embodiments of the invention, the anthracenedione is selected from the group consisting of mitoxantrone, pixantrone, ametantrone, and piroxantrone.

According to some embodiments of the invention, the chemotherapeutic agent is capable of accumulating within lysosomes of the proliferating cells.

According to some embodiments of the invention, the hydrophobic weak base is characterized by a pKa in a range of from 5 to 12, the pKa representing a transition between a neutrally charged state and a positively charged state.

According to some embodiments of the invention, the neutrally charged state of the hydrophobic weak base is characterized by a logP value of at least 0.5.

According to some embodiments of the invention, the chemotherapeutic agent acts as a photosensitizer when exposed to illumination at a wavelength in a range of from 400 to 800 nm.

According to some embodiments of the invention, the chemotherapeutic agent is administered at a dosage which is 20% or less than a cytotoxic dosage of the chemotherapeutic agent.

According to some embodiments of the invention, the chemotherapeutic agent is effected by intravenous injection or by topical administration.

According to some embodiments of the invention, the illumination is characterized by a fluence in a range of from 2 to 1000 $J/cm^2$.

According to some embodiments of the invention, the disease or disorder is selected from the group consisting of cancer and hyperplasia.

According to some embodiments of the invention, the region of the body comprises a tumor.

According to some embodiments of the invention, the cancer is a multidrug resistant cancer.

According to some embodiments of the invention, a method described hereinabove further comprises administering chloroquine to the subject prior to the illuminating.

According to some embodiments of the invention, the chemotherapeutic agent is for use in combination with chloroquine.

According to some embodiments of the invention, the medicament is further identified for use in combination with chloroquine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a scheme presenting the structural formulas of exemplary imidazoacridinones;

Figure 2:
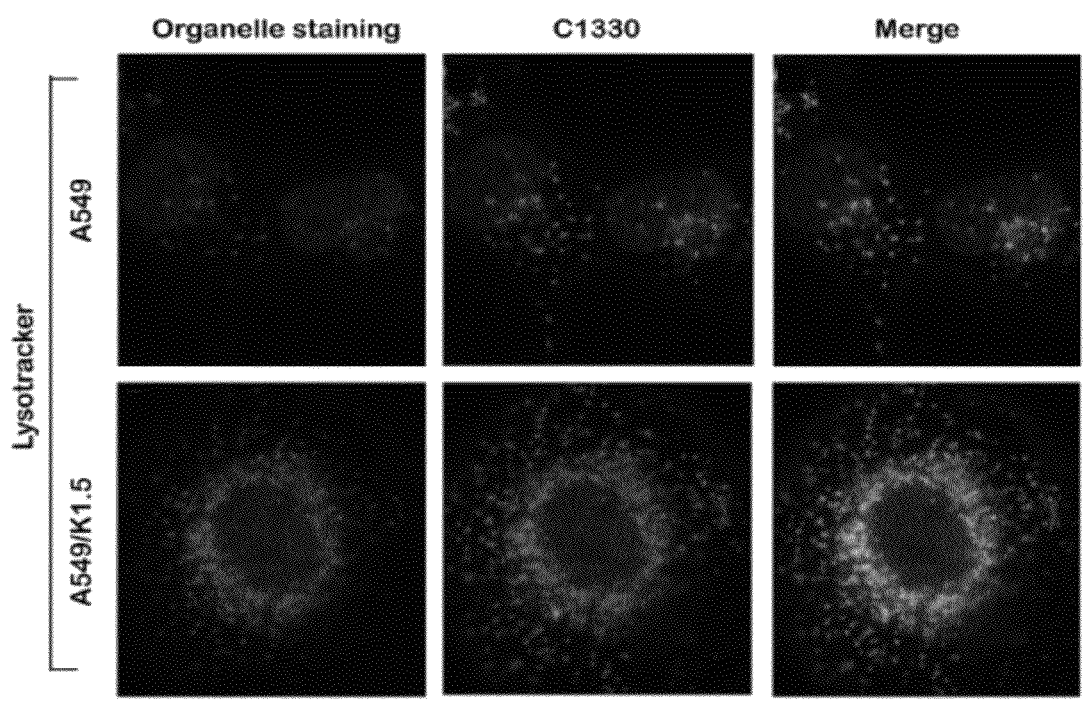
Figure 3:
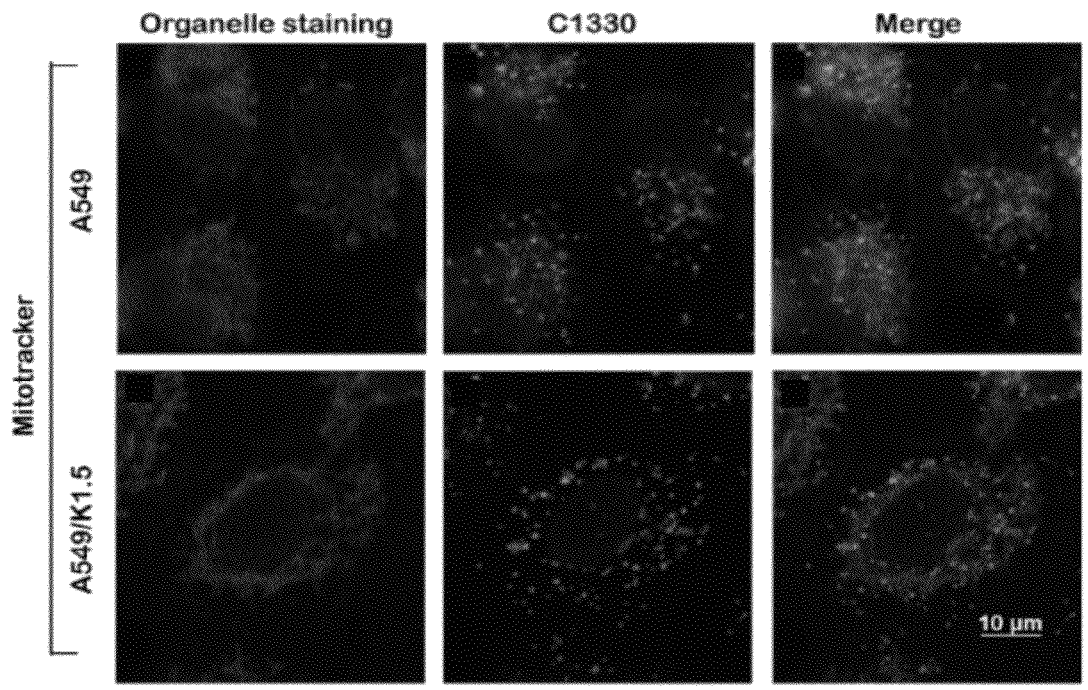
Figure 4:
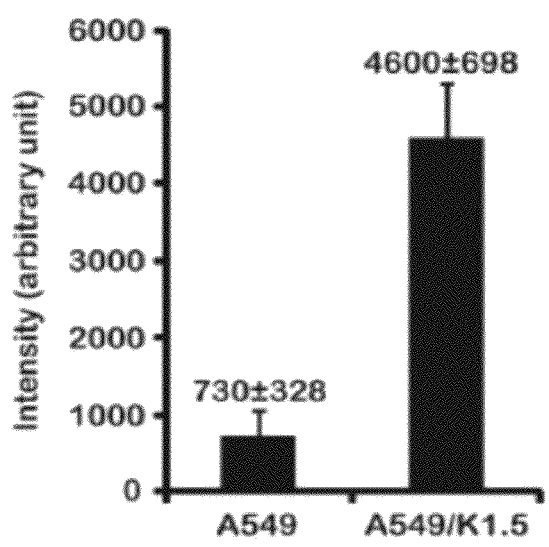
Figure 5:
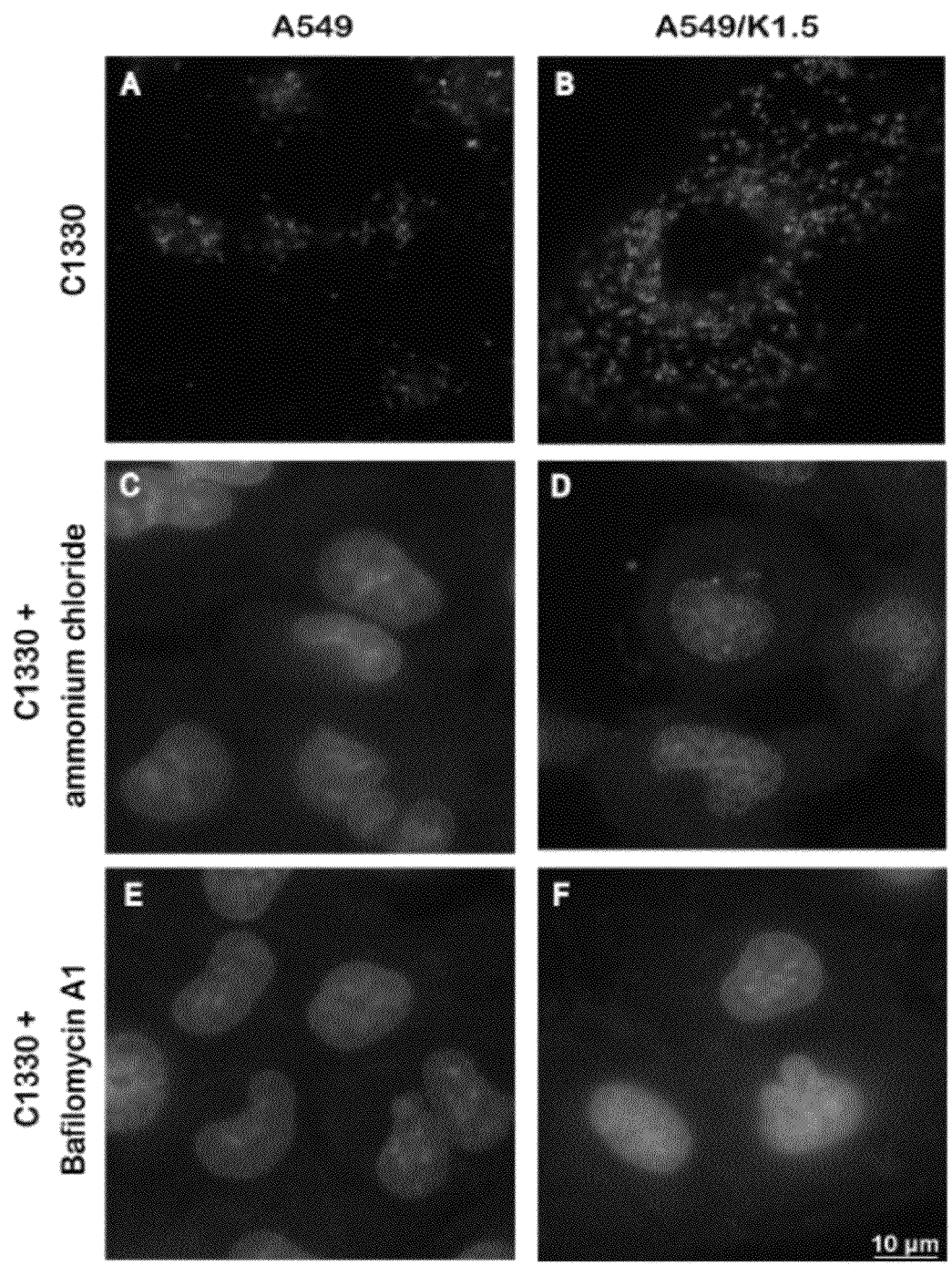
Figure 7A:
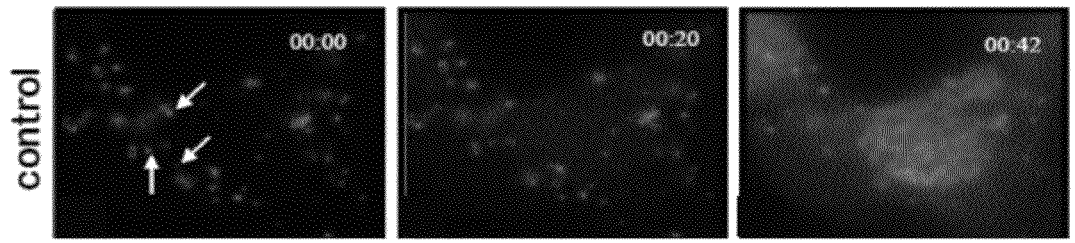
Figure 8A:
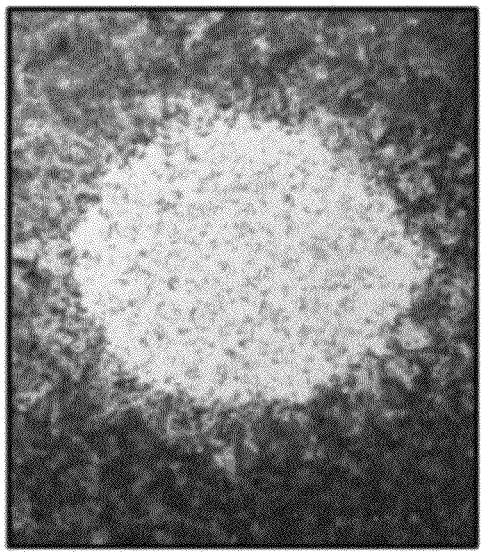
Figure 8B:
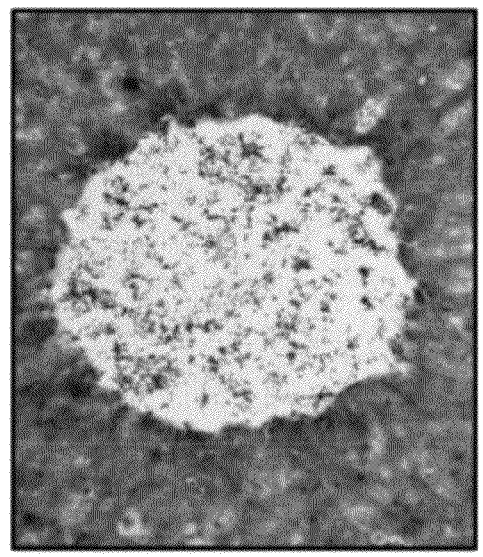
Figure 8C:
Figure 9A:
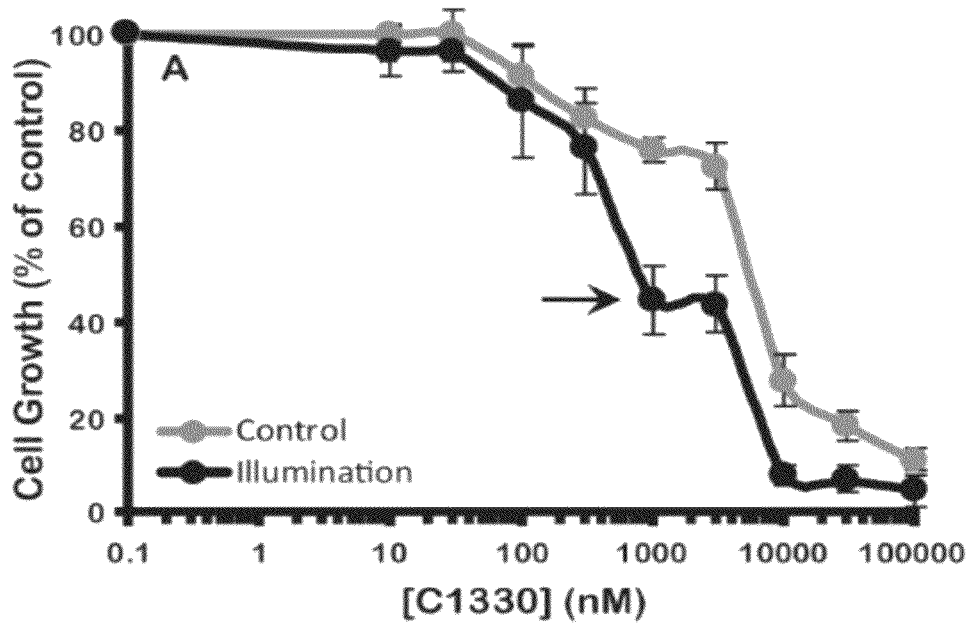
Figure 9B:
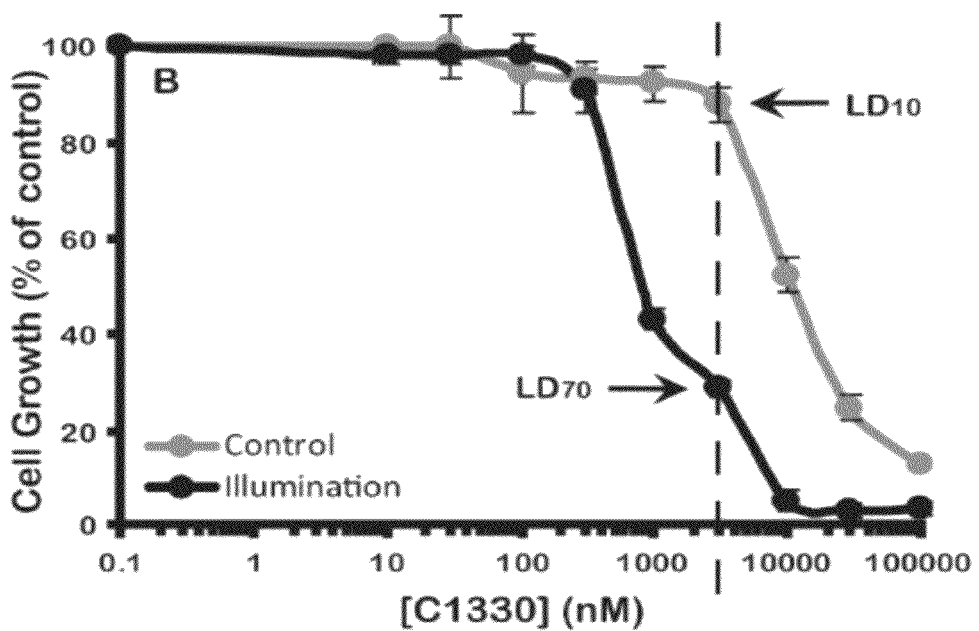
Figure 10A:
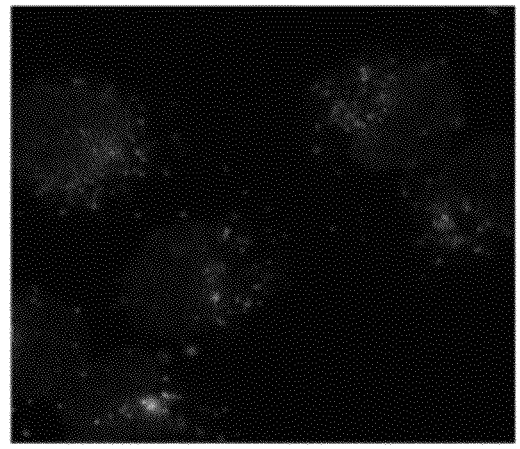
Figure 10B:
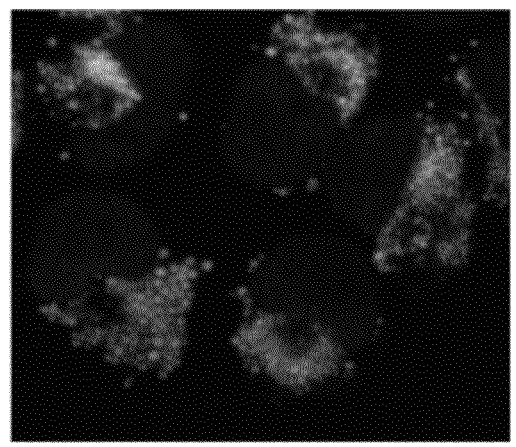
Figure 10C:
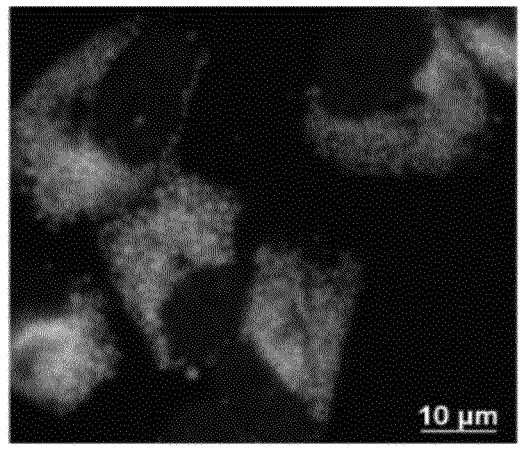
Figure 11:
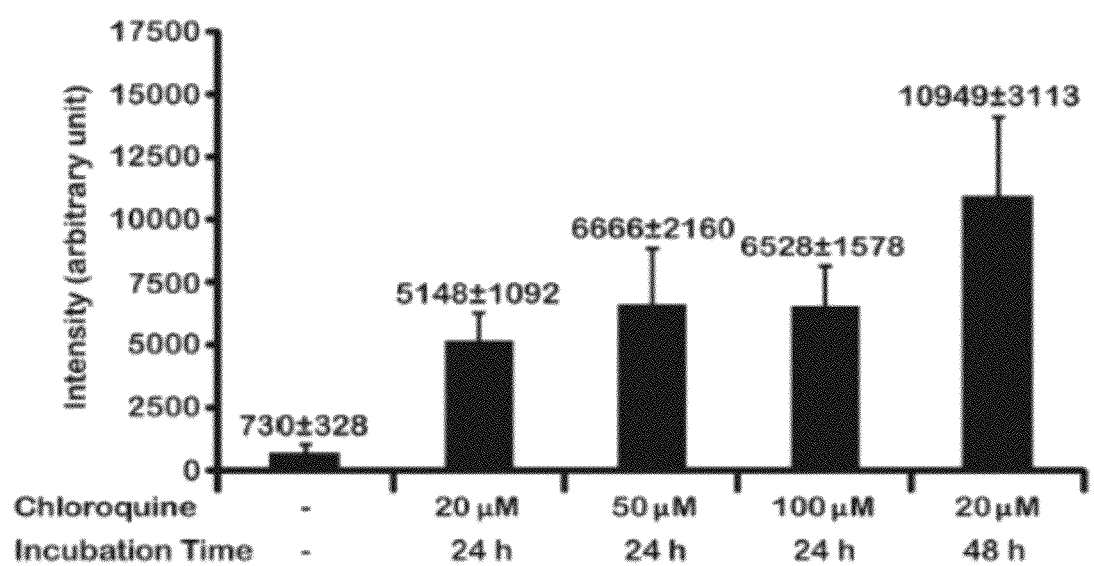
Figure 12A:
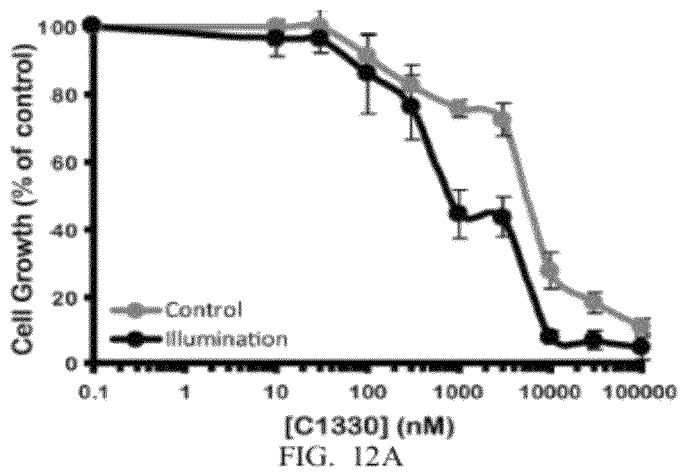
Figure 12B:
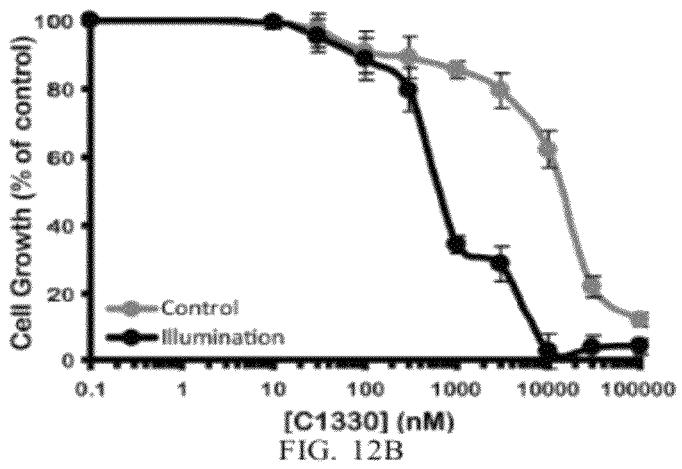
Figure 12C:
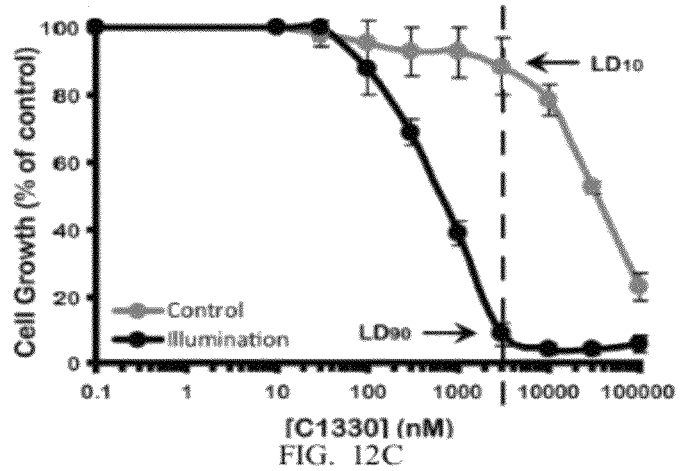
Figure 13A:
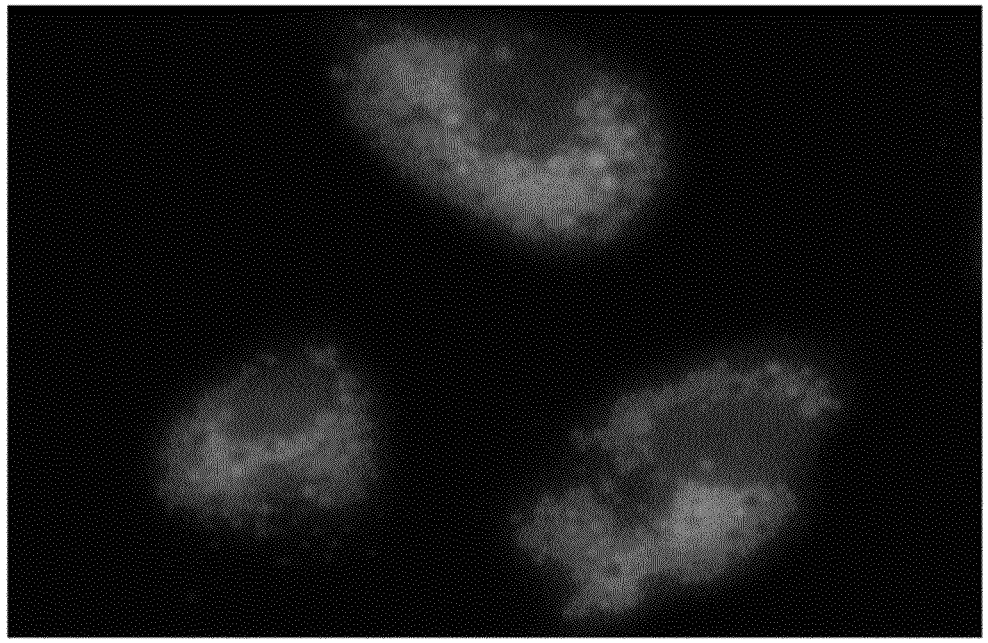
Figure 13B:
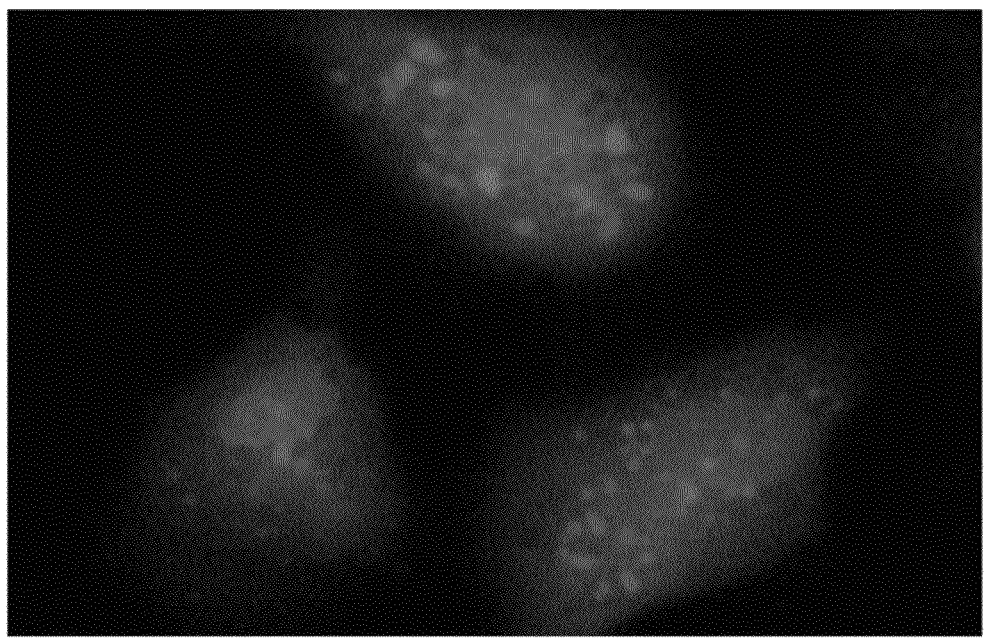
Figure 15A:
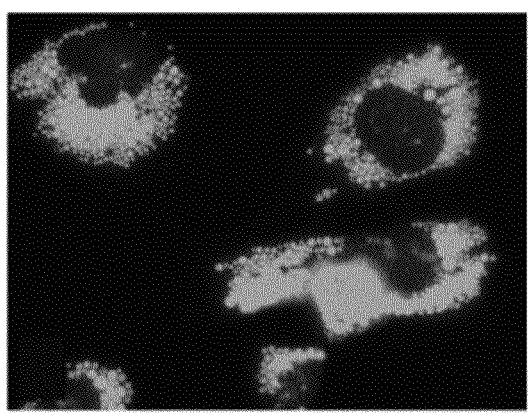
Figure 15B:
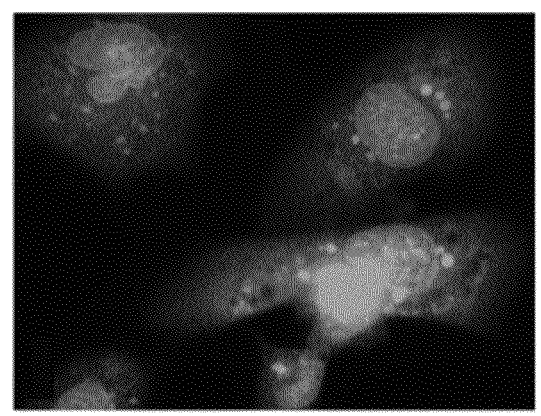
Figure 16:
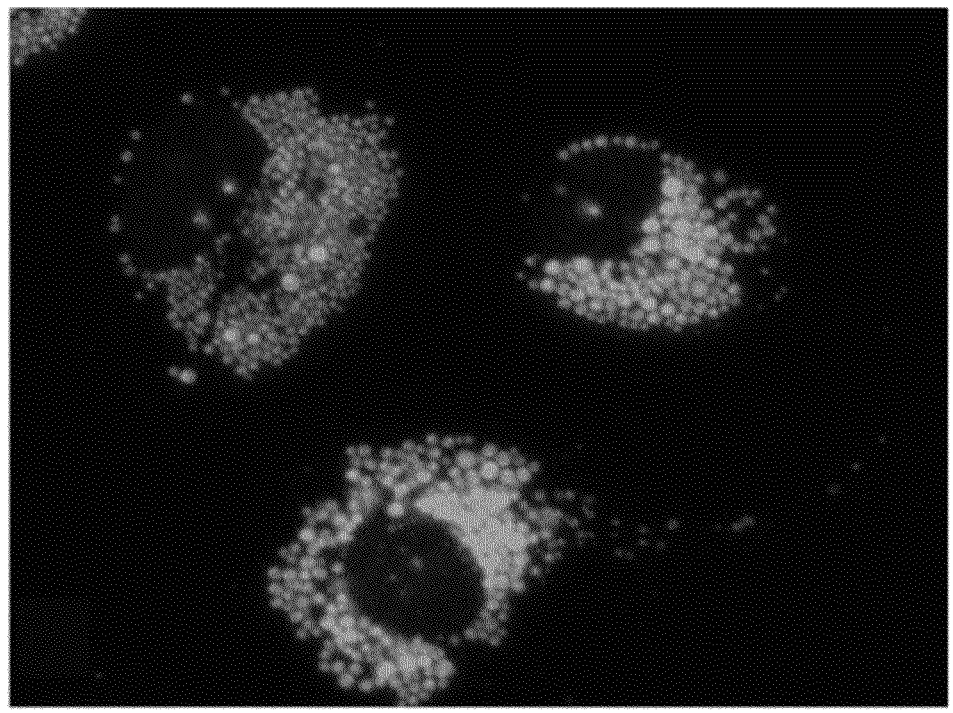
Figure 17:
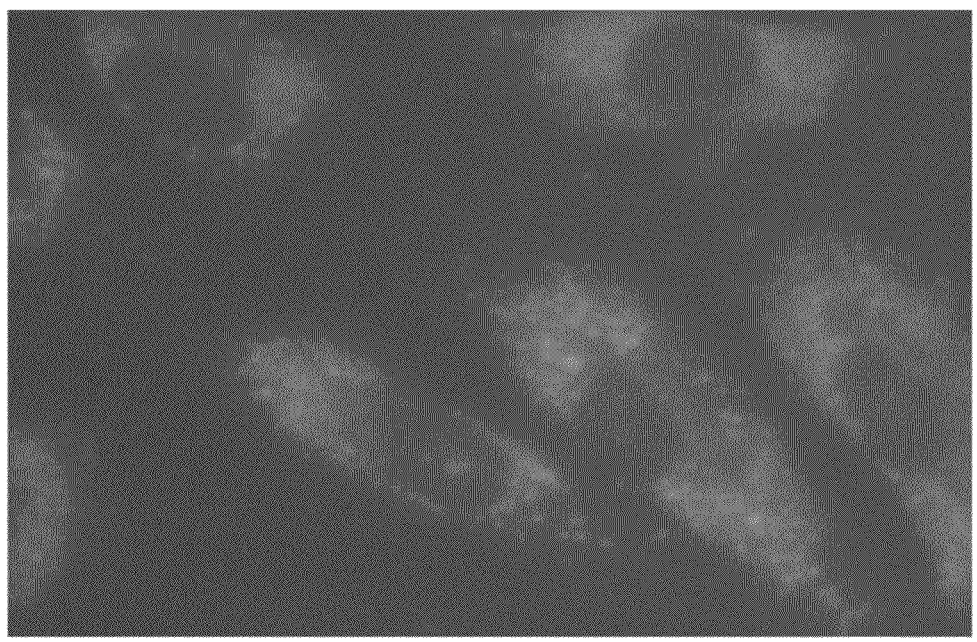
Figure 18:
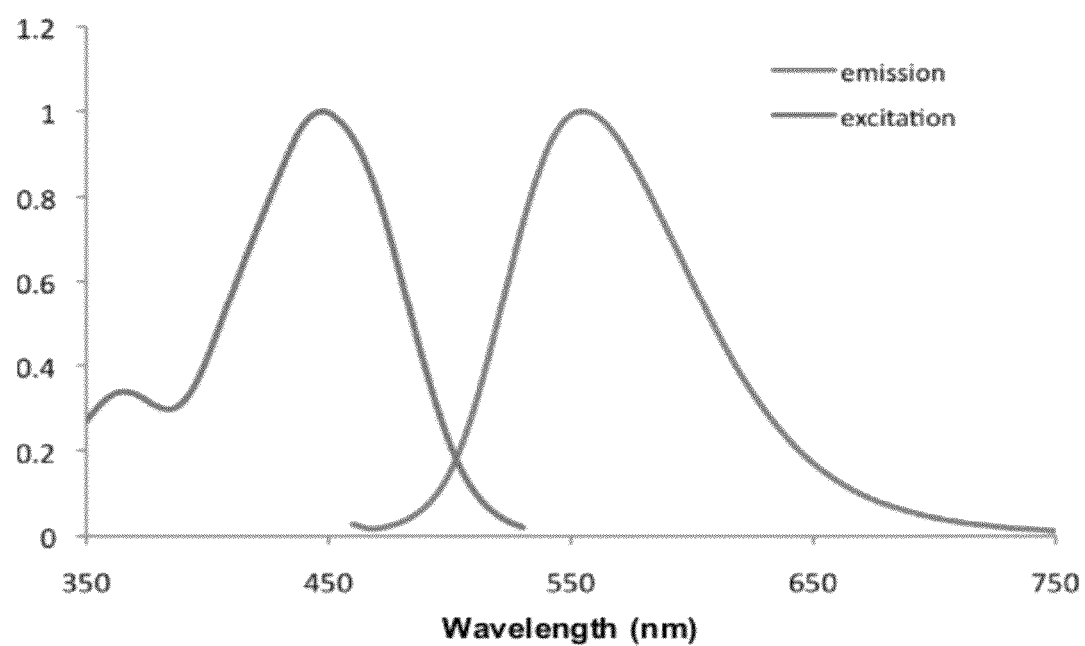
Figure 19A:
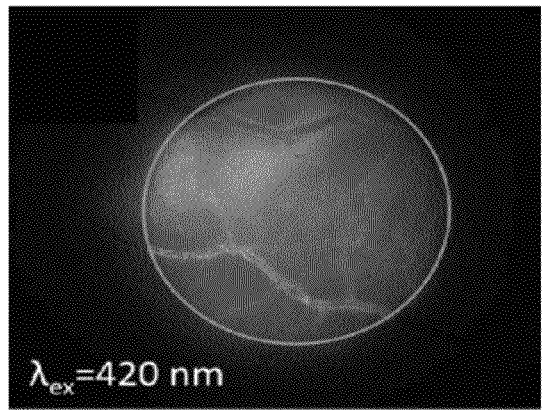
Figure 19B:
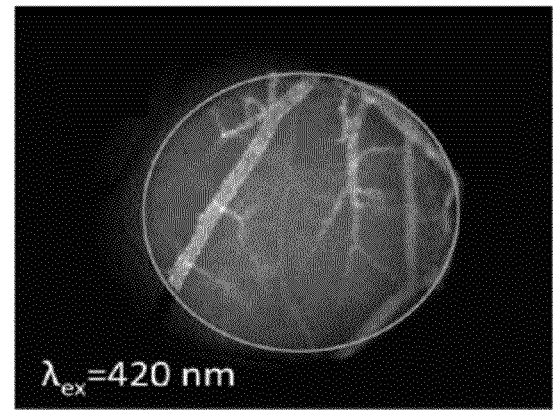
Figure 19C:
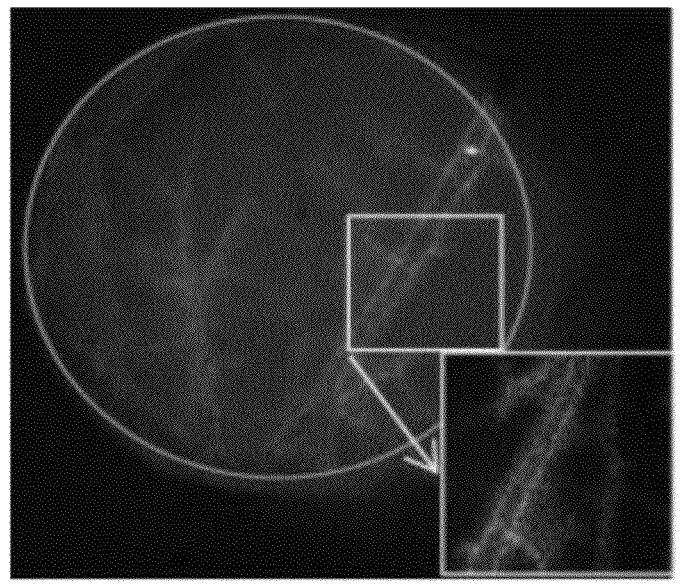
Figure 20A:
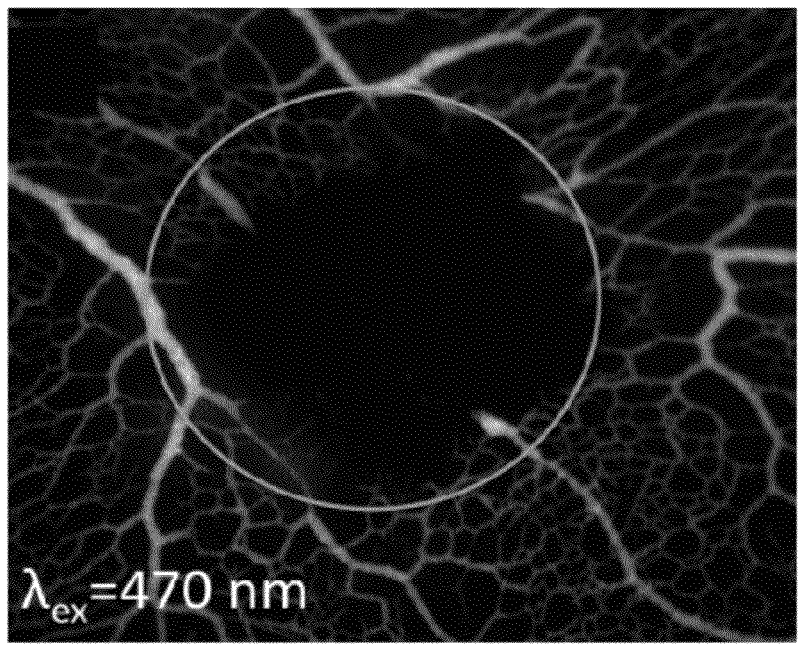
Figure 20B:
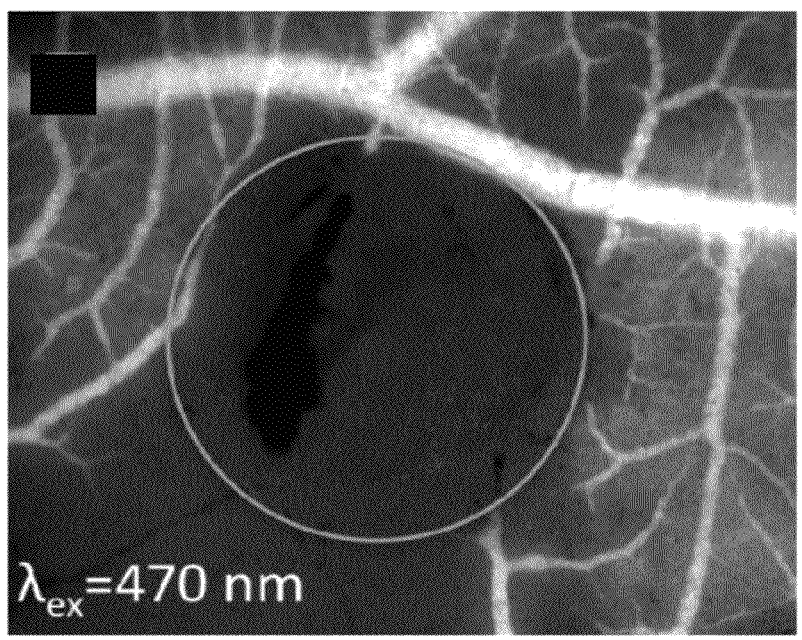
Figure 21A:
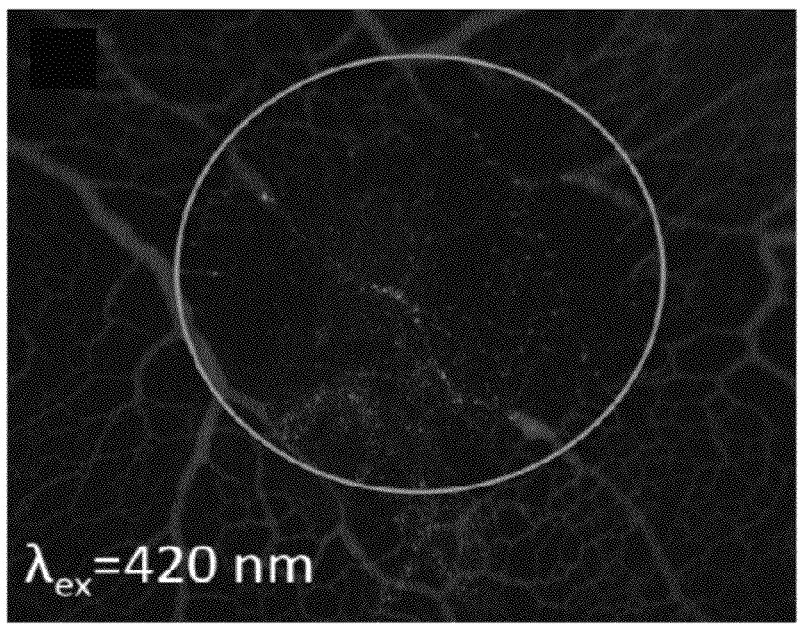
Figure 21B:
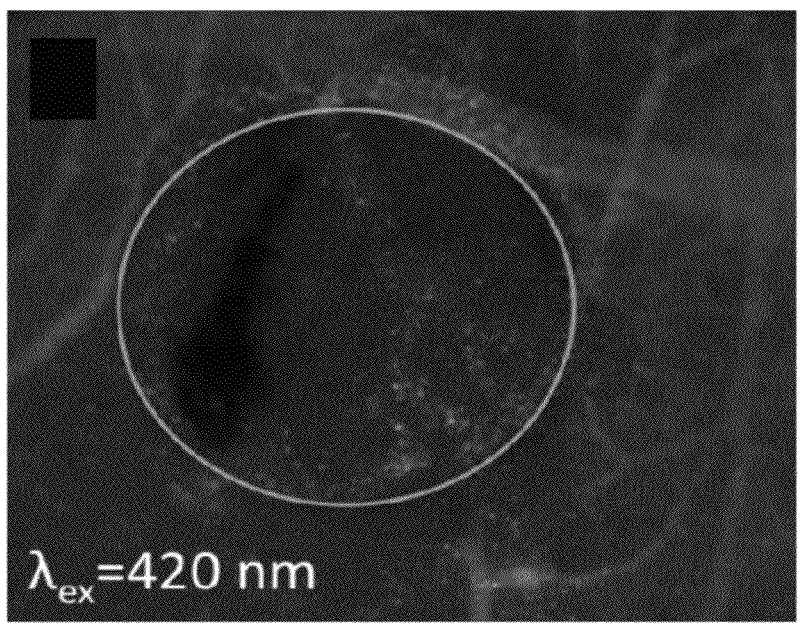
Figure 22A:
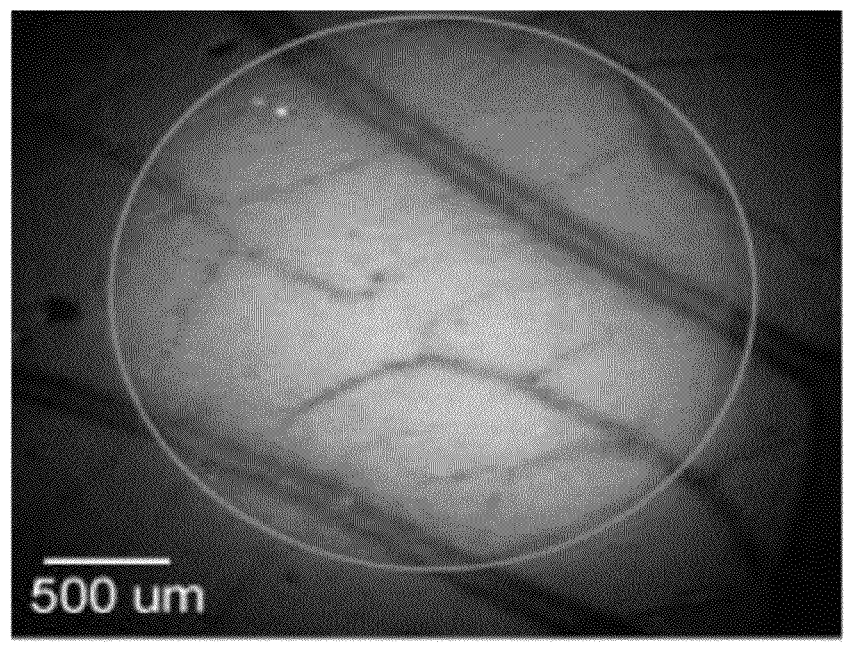
Figure 22B:
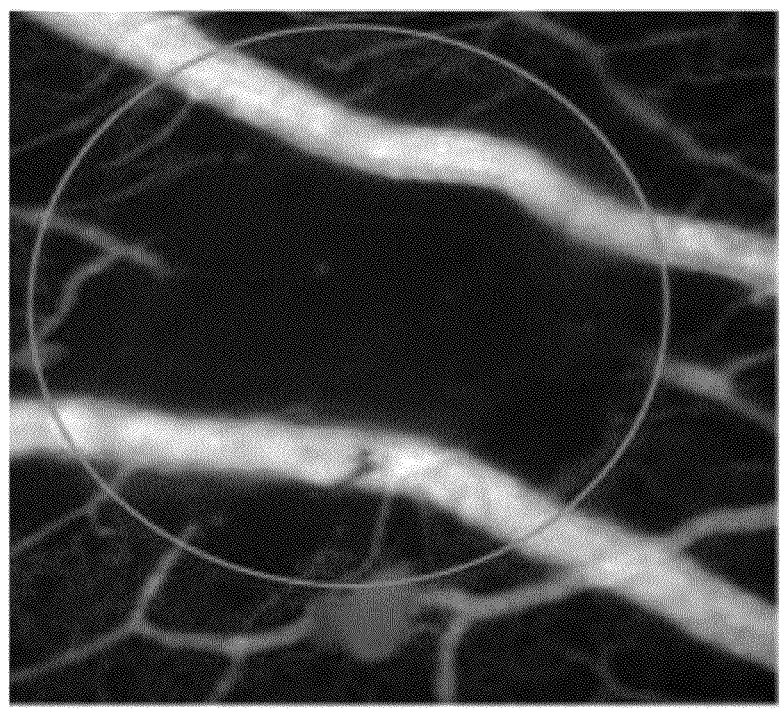
Figure 23A:
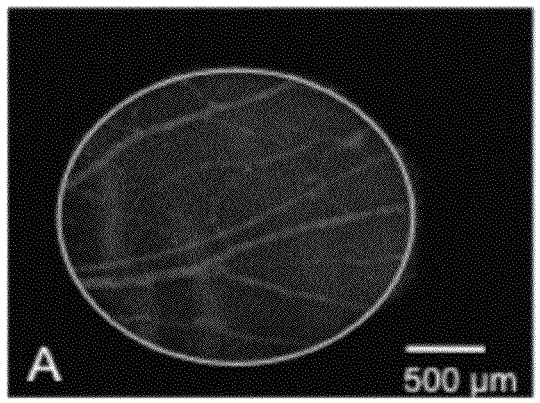
Figure 23B:
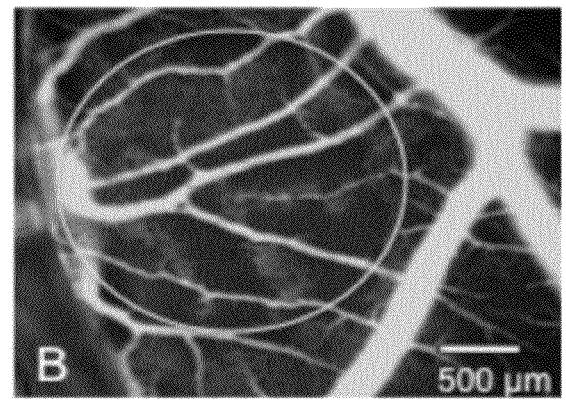
Figure 23C:
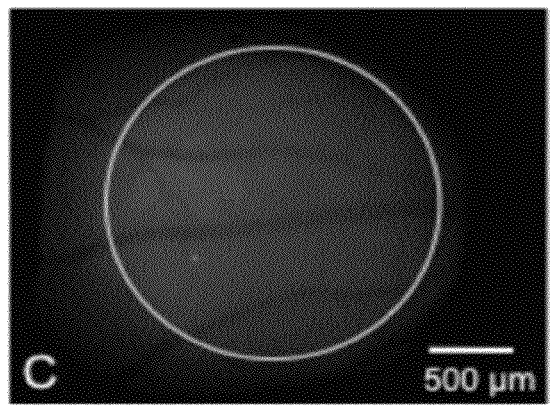
Figure 23D:
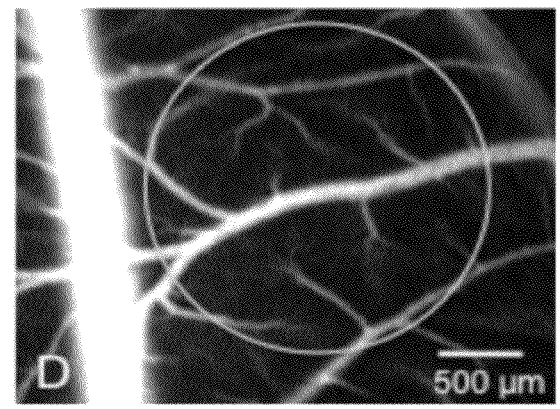
Figure 25A:
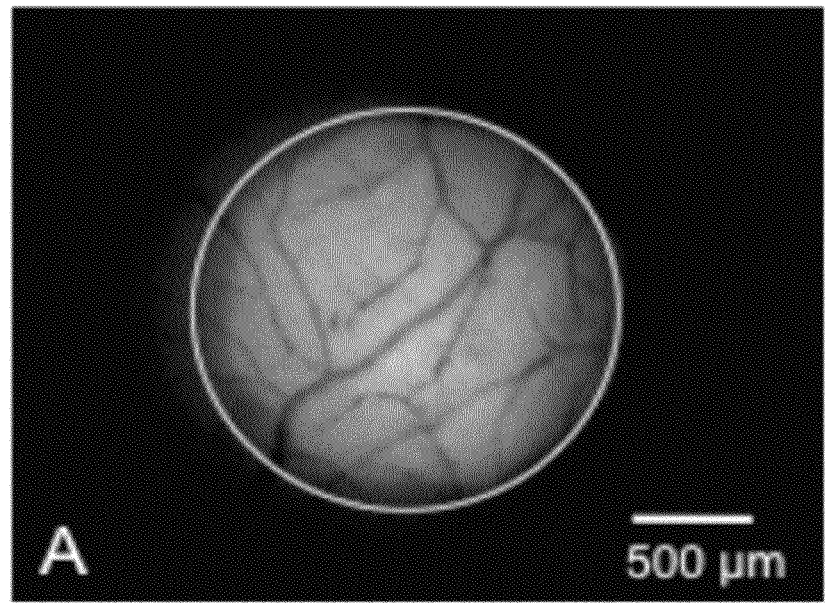
Figures 25B, 25C:
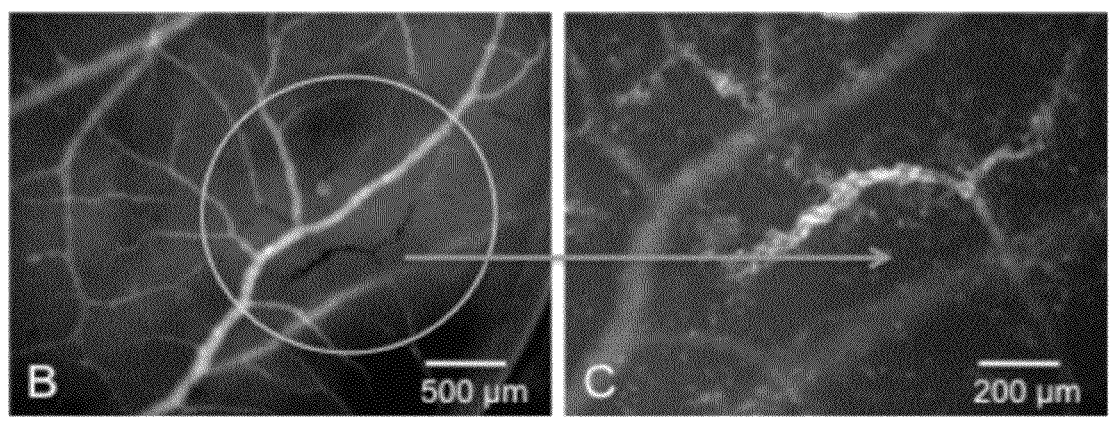
Figure 26A:
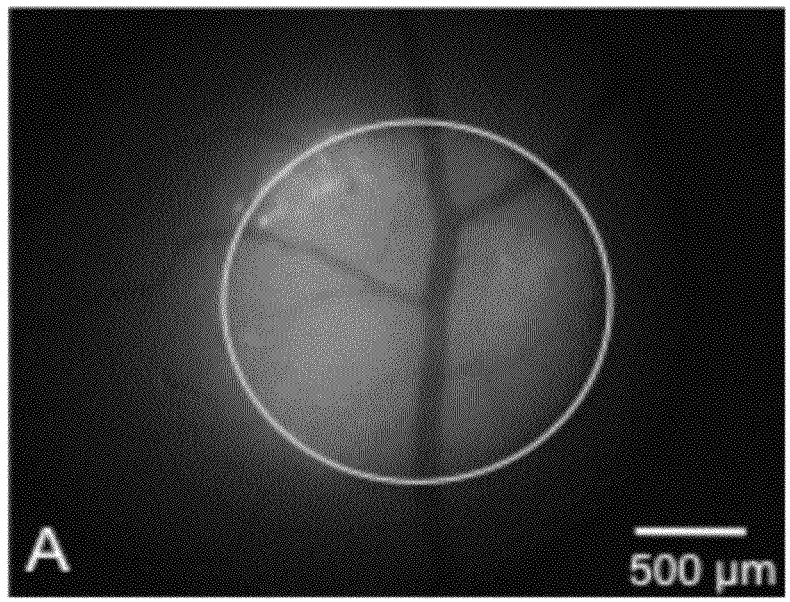
Figure 26B:
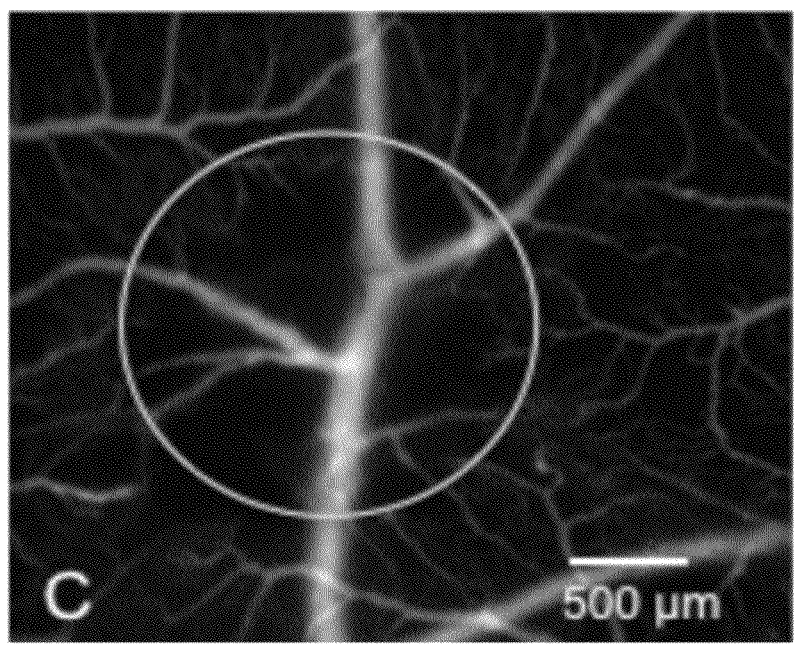
Figure 27A:
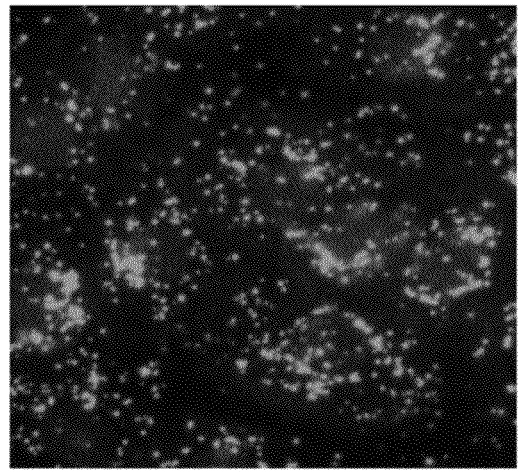
Figure 27B:
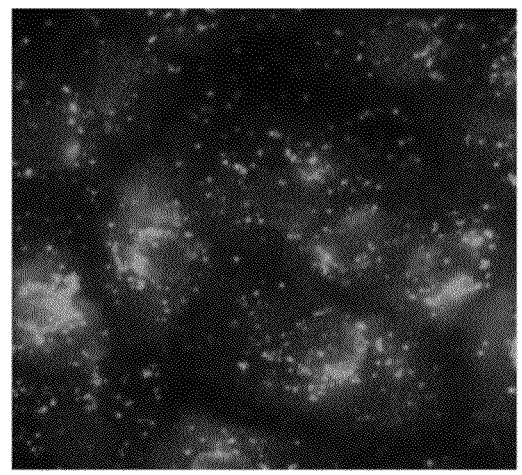
Figure 27C:
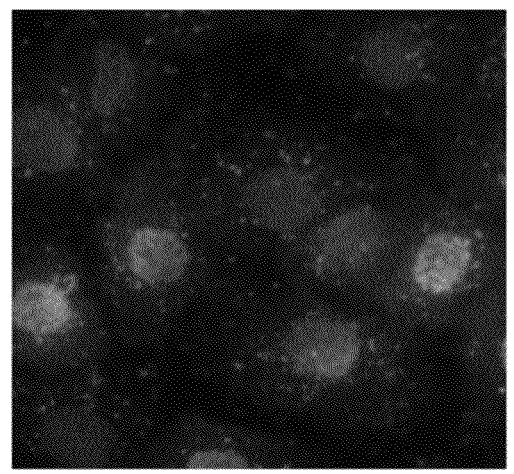
Figure 30A:
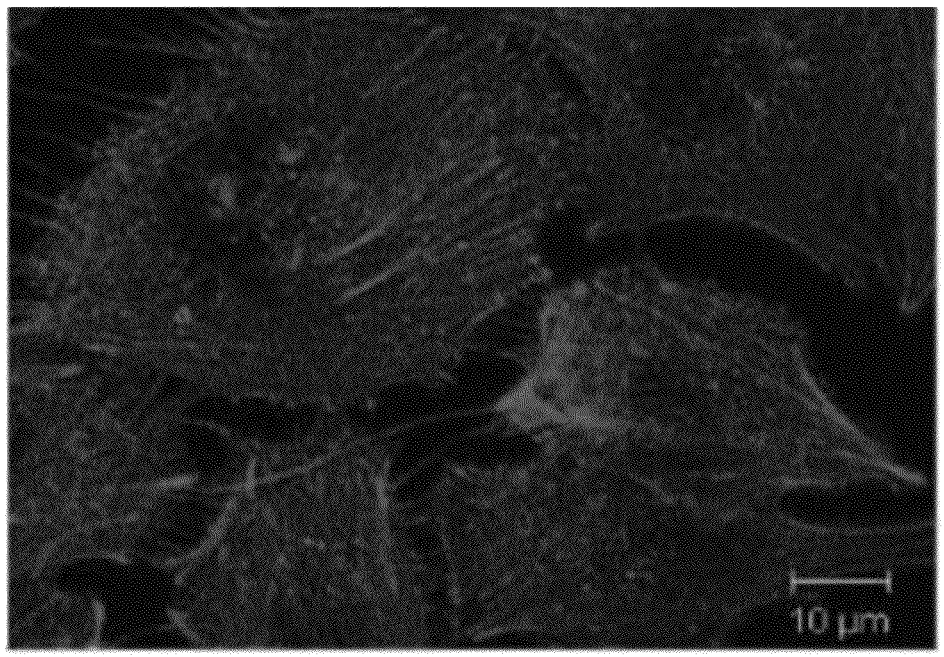
Figure 30B:
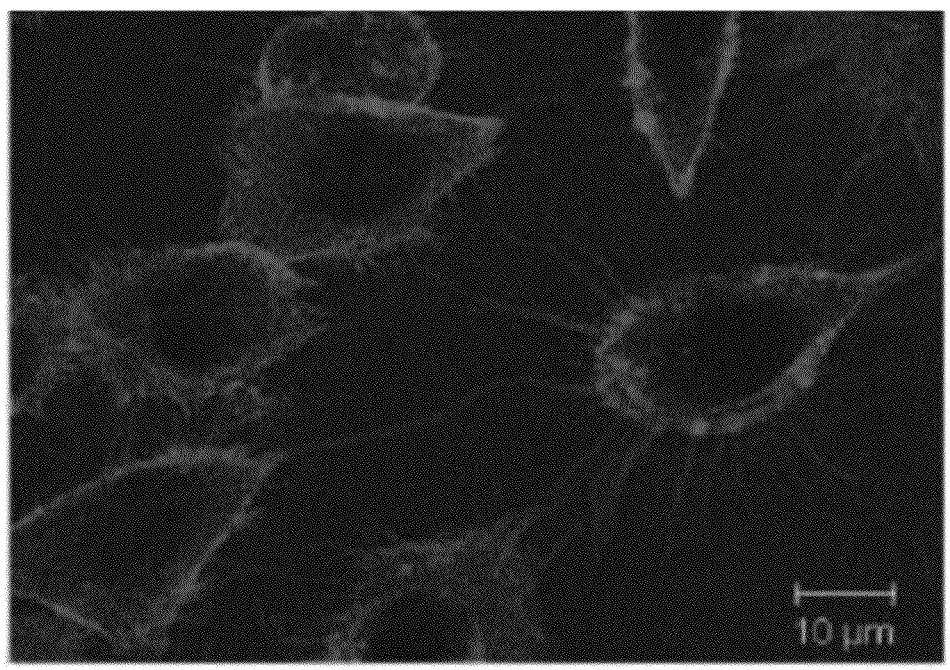
Figure 31:
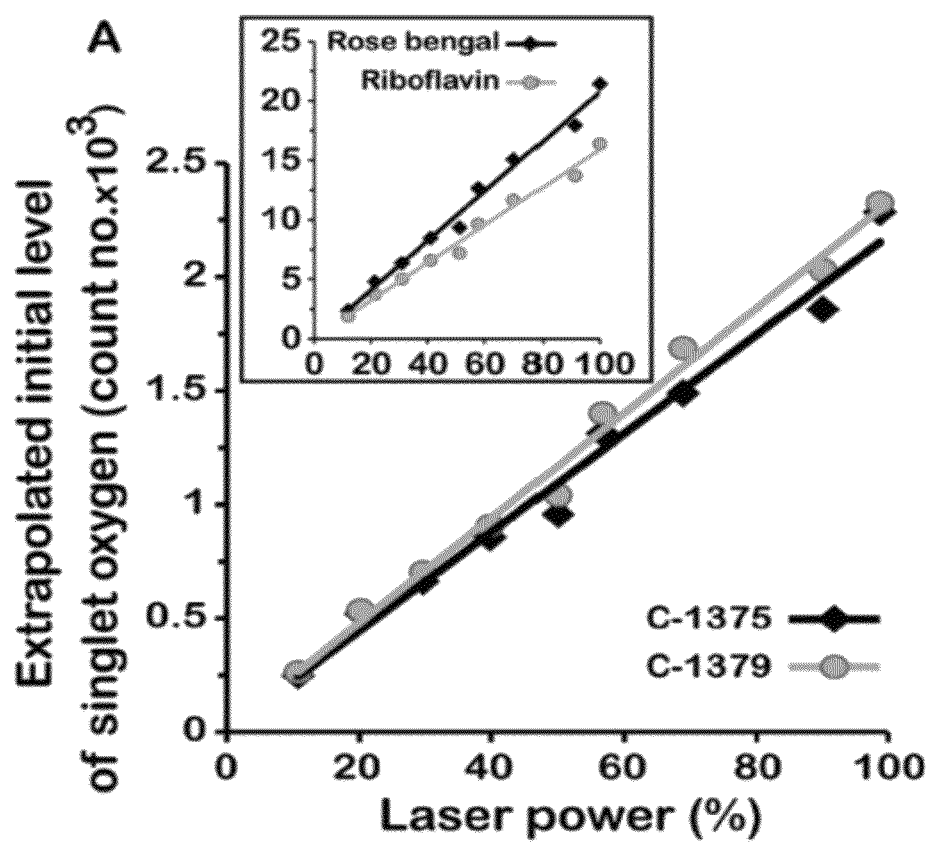
Figure 32:
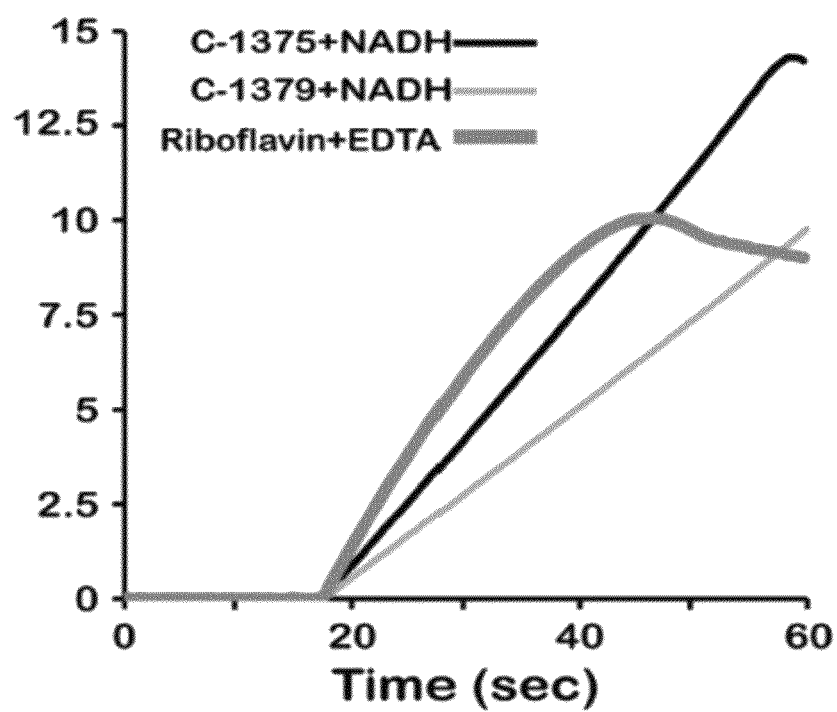

FIG. 2 presents images showing the red fluorescence of lysosomes viably stained by LysoTracker® Red (Organelle staining) and the green fluorescence of C-1330, an exemplary imidazoacridinone according to some embodiments of the present invention, as well as images showing both LysoTracker® Red and C-1330 fluorescence (Merge), in parental human lung cancer A549 cells and their multidrug resistant A549/K1.5 subline (blue fluorescence indicates Hoechst 33342 staining of nuclei, magnification is ×630);

FIG. 3 presents images showing the red fluorescence of mitochondria viably stained by MitoTracker® Red (Organelle staining) and the green fluorescence of C-1330, as well as images showing both MitoTracker® Red and C-1330 fluorescence (Merge), in parental A549 cells and in multidrug resistant A549/K1.5 cells (blue fluorescence indicates Hoechst 33342 staining of nuclei, magnification is ×630);

FIG. 4 is a bar graph quantifying the amount of lysosomes in A549 and A549/K1.5 cells, as determined by LysoTracker® Red fluorescence;

FIG. 5 presents images showing C-1330 fluorescence in A549 cells and A549/K1.5 cells following pretreatment with ammonium chloride (10 mM) or bafilomycin A1 (1 μM) or without any pretreatment (upper row) (magnification is ×630);

FIGS. 6A-6F present images showing C-1330 fluorescence in A549 cells (FIGS. 6A-6C) and A549/K1.5 cells (FIGS. 6D-6F) at the initiation of blue light illumination (FIGS. 6A and 6D), after photodestruction of some lysosomes by blue light illumination (FIGS. 6B and 6E), and after photodestruction of nearly all lysosomes by further blue light illumination (magnification is ×630); the area within the white squares is shown enlarged (upper panels of FIGS. 6A-6C and lower panels of FIGS. 6D-6F);

FIGS. 7A-7D present images showing C-1330 fluorescence in A549 cells upon blue light illumination for various time periods (time indicated in seconds in each image), following pretreatment for 1 hour with 50 mM dimethylthiourea (FIG. 7B), 10 mM L-histidine (FIG. 7C) or 50 mM sodium azide (FIG. 7D), or without pretreatment (FIG. 7A); white arrows in FIG. 7A indicate lysosomes which disappear at later times (magnification is ×630);

FIGS. 8A-8C are images showing C-1330-loaded monolayers of A549 (FIGS. 8A and 8C) and A549/K1.5 (FIG. 8B) cells stained by crystal violet 48 hours after illumination by a beam of blue (470 nm) light; the illuminated area is visible as a region of lysed cells surrounded by intact cells in the non-illuminated area (magnification is ×8 in FIGS. 8A and 8B, ×1000 in FIG. 8C);

FIGS. 9A and 9B are graphs showing the viability of parental A549 cells (FIG. 9A) and multidrug resistant A549/K1.5 cells (FIG. 9B) as a function of C-1330 concentration, in the presence or absence (control) of illumination (white light, 100 J/m$^2$) (values represent mean±standard deviation of at least 3 independent experiments); FIG. 9B indicates (dotted line) a concentration at which cell death is approximately 10% ($LD_{10}$) without illumination and 70% ($LD_{70}$) with illumination;

FIGS. 10A-10C are images showing lysosomes stained by LysoTracker® Red (orange fluorescence) in A549 cells incubated in the absence (FIG. 10A) or presence (FIGS. 10B and 10C) of 20 μM chloroquine for 24 (FIG. 10B) or 48 (FIG. 10C) hours (blue fluorescence indicates Hoechst 33342 staining of nuclei, magnification is ×630);

FIG. 11 is a bar graph showing the amount of lysosomes in A549 cells, as determined by LysoTracker® Red fluorescence, following incubation with 20, 50 or 100 μM chloroquine for 24 or 48 hours (control cells not incubated with chloroquine);

FIGS. 12A-12C are graphs showing the viability of A549 cells incubated in the absence (FIG. 12A) or presence (FIGS. 12B and 12C) of 20 μM chloroquine for 24 hours (FIG. 10B) or 48 (FIG. 10C) hours, in the presence or absence (control) of illumination (white light, 100 J/m$^2$), as a function of C-1330 concentration (values represent mean±standard deviation of at least 3 independent experiments); FIG. 12C indicates (dotted line) a concentration at which cell death is approximately 10% ($LD_{10}$) without illumination and 90% ($LD_{90}$) with illumination;

FIGS. 13A and 13B present images showing fluorescence of C-1375, another exemplary imidazoacridinone according to some embodiments of the present invention, in human umbilical vein endothelial cells (HUVEC) at the initiation of blue light illumination (FIG. 13A) and after 1 minute of blue light (420 nm) illumination (FIG. 13B);

FIGS. 14A-14D present images showing fluorescence of C-1375 in human umbilical vein endothelial cells (HUVEC) at the initiation of blue light illumination (FIG. 13A) and after 40 seconds (FIG. 14B), 67 seconds (FIG. 14C) and 127 seconds (FIG. 14D) of blue light illumination;

FIGS. 15A and 15B present images showing fluorescence of C-1375 in human dermis-derived endothelial cells (HMEC) following 6 seconds (FIG. 15A) and 90 seconds (FIG. 15B) of blue light (420 nm) illumination;

FIG. 16 presents an image showing fluorescence of C-1375 in RF24 endothelial cells;

FIG. 17 presents an image showing fluorescence of sunitinib, an exemplary chemotherapeutic agent according to some embodiments of the present invention, in human umbilical vein endothelial cells (HUVEC);

FIG. 18 is a graph showing the excitation and emission spectra of C-1379, another exemplary imidazoacridinone according to some embodiments of the present invention (y-axis is normalized such that peak values equal 1);

FIGS. 19A-19C show fluorescence of C-1379 (FIGS. 19A and 19C) and C-1375 (FIG. 19B) in chicken chorioallantoic membrane (CAM) vasculature, at the initiation (FIGS. 19A and 19B) and at the end (FIG. 19C) of blue light (420 nm, 20 J/cm$^2$) illumination (red circle indicates illuminated region, inset at lower-right corner of FIG. 19C shows the area in square at a higher magnification);

FIGS. 20A and 20B show fluorescence (excitation wavelength=470 nm) of fluorescein isothiocyanate (FITC)-dextran in CAM vasculature, 24 hours after injection of C-1379 (FIG. 20A) or C-1375 (FIG. 20B) and blue light illumination (420 nm, 20 J/cm$^2$) (red circle indicates illuminated region);

FIGS. 21A and 21B show fluorescence (excitation wavelength=420 nm) of C-1379 (FIG. 21A) and C-1375 (FIG. 21B), visible as bright points, in CAM vasculature, 24 hours after injection of C-1379 or C-1375 and blue light illumination (420 nm, 20 J/cm$^2$) (red circle indicates illuminated region);

FIGS. 22A and 22B present angiography images of CAM vasculature showing C-1379 fluorescence (FIG. 22A, excitation wavelength 420 nm) and FITC-dextran fluorescence (FIG. 22B, excitation wavelength 470 nm) immediately before (FIG. 22A) or 24 hours after (FIG. 22B) blue light illumination (420 nm, 20 J/cm$^2$), in the presence of intravenously injected 1 µg/embryo of C-1379 (red circle indicates illuminated region);

FIGS. 23A-23D present angiography images of CAM vasculature showing sunitinib fluorescence (FIG. 23A, excitation wavelength 420 nm), FITC-dextran fluorescence (FIGS. 23B and 23D, excitation wavelength 470 nm) or auto-fluorescence (FIG. 23C, excitation wavelength 420 nm) immediately before (FIGS. 23A and 23C) or 24 hours after (FIGS. 23B and 23D) blue light illumination (420 nm, 130 J/cm$^2$) in the presence (FIGS. 23A and 23B) or absence (FIGS. 23C and 23D) of 0.002 µg/embryo of intravenously injected sunitinib (red circle indicates illuminated region);

FIGS. 24A-24E present angiography images of CAM vasculature showing sunitinib fluorescence (FIGS. 24A and 24B, excitation wavelength 420 nm), FITC-dextran fluorescence (FIGS. 24C and 24E, excitation wavelength 470 nm) or auto-fluorescence (FIG. 24D, excitation wavelength 420 nm) immediately before (FIGS. 24A and 24D), immediately after (FIG. 24B) or 24 hours after (FIGS. 24C and 24E) blue light illumination (420 nm, 130 J/cm$^2$) in the presence (FIGS. 24A-24C) or absence (FIGS. 24D and 24E) of 12 µg/embryo of intravenously injected sunitinib (red circle indicates illuminated region);

FIGS. 25A-25C present angiography images of CAM vasculature showing CAM autofluorescence (FIG. 25A, excitation wavelength 420 nm), sunitinib fluorescence (FIG. 25C, excitation wavelength 420 nm), or FITC-dextran fluorescence (FIG. 25B, excitation wavelength 470 nm) immediately before (FIG. 25A) or 24 hours after (FIGS. 25B and 25C) blue light illumination (420 nm, 130 J/cm$^2$) in the presence of 200 µg/embryo of intravenously injected sunitinib (red circle indicates illuminated region, FIG. 25C shows a portion of the illuminated region at a higher magnification);

FIGS. 26A and 26B present angiography images of CAM vasculature showing sunitinib fluorescence (FIG. 26A, excitation wavelength 420 nm) or FITC-dextran fluorescence (FIG. 26B, excitation wavelength 470 nm) immediately before (FIG. 26A), or 24 hours after (FIG. 26B) blue light illumination (420 nm, 130 J/cm$^2$) in the presence of 40 µg/embryo of topically administered sunitinib (red circle indicates illuminated region);

FIGS. 27A-27C present images showing doxorubicin fluorescence in A549/K1.5 cells at the initiation of blue light illumination (FIG. 27A), after photodestruction of some lysosomes by 10 seconds of blue light illumination (FIG. 27B), and after photodestruction of nearly all lysosomes by 20 seconds of blue light illumination;

FIGS. 28A-28F present angiography images of human A2780 ovarian carcinoma tumors showing C-1379 fluorescence (FIGS. 28A and 28D) or FITC-dextran fluorescence (FIGS. 28B, 28C, 28E and 28F) immediately after (FIGS. 28A and 28D), 24 hours after (FIGS. 28B and 28E) and 72 hours after (FIGS. 28C and 28F) intravenous injection of C-1379, with illumination (34 J/cm$^2$) 1 minute and 24 hours after C-1379 injection (FIGS. 28A-28C) or without illumination (FIGS. 28D-28F);

FIGS. 29A-29D present photographs of human A2780 ovarian carcinoma tumors 24 hours after (FIGS. 29A and 29C) and 72 hours after (FIGS. 29B and 29D) intravenous injection of C-1379, with illumination (34 J/cm$^2$) 1 minute and 24 hours after C-1379 injection (FIGS. 29A and 29B) or without illumination (FIGS. 29C and 29D);

FIGS. 30A and 30B present images showing F-actin of A549 cells stained by Texas Red®-X Phalloidin, upon incubation for 30 minutes with 10 µM C-1330, 2 hours after illumination (FIG. 30B) or without illumination (FIG. 30A);

FIG. 31 is a graph showing singlet oxygen luminescence counts after laser irradiation of C-1375, C-1379, Rose Bengal and riboflavin, as a function of laser power; and FIG. 32 is a graph showing the amplitude (in arbitrary units) of an EPR signal for a superoxide spin adduct as a function of time; the rise in amplitude indicates the beginning of illumination of the samples (C-1375 with NADH; C-1379 with NADH; or riboflavin with EDTA).

DESCRIPTION OF SPECIFIC EMBODIMENTS
OF THE INVENTION

The present invention, in some embodiments thereof, relates to therapy and, more particularly, but not exclusively, to novel methodologies for treating medical conditions such as proliferative diseases and disorders, and drug resistant as well as multidrug resistant (MDR) conditions in particular.

Embodiments of the present invention are based on the findings that hydrophobic weak base compounds, including chemotherapeutic agents such as IAs, efficiently accumulate within lysosomes, and that illumination of cells loaded with such agents which are furthermore chromophoric results in rupture of lysosomes and cell death.

The chromophoricity (i.e., absorption of visible light) was hypothesized to be necessary for activation by visible light, and a hydrophobic weak base was hypothesized to be suitable for accumulating in lysosomes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
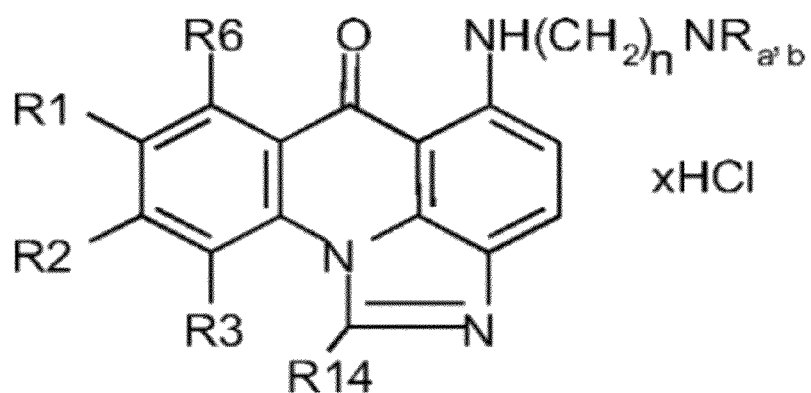

Referring now to the drawings, FIG. 1 presents the structural formulas of exemplary imidazoacridinones (IAs). FIG. 18 shows the excitation and emission spectra of fluorescence of C-1375, an exemplary IA.

FIG. 2 shows that C-1330, an exemplary IA, accumulates primarily in the lysosomes of cancer cells, whereas FIG. 3 shows that C-1330 does not accumulate to a significant degree in the mitochondria. FIGS. 13A, 14A, 15A and 16 show that C-1375, another exemplary IA, also accumulates primarily in the lysosomes of cancer cells.

FIG. 4 shows that multi-drug resistant cancer cells contain considerably more lysosomes than do their non-resistant parental cancer cells.

FIG. 5 shows that when the acidity of lysosomes is reduced by a lysosomotropic alkalinization agent such as ammonium chloride or bafilomycin A1, the IA accumulates in the nuclei of cells instead of in lysosomes.

FIGS. 6A-6F and 13A-15B show that upon illumination IAs exit individual lysosomes in sudden bursts, until nearly all of the IA has exited the lysosomes and accumulated in the nucleus. This was observed in both cancer cells (FIGS. 6A-6F) and in endothelial cells (FIGS. 13A-15B). This result indicates that lysosomes containing the IA are ruptured when exposed to illumination. FIGS. 7A-7D show that the rupture of lysosomes is partially inhibited by scavengers of reactive oxygen species. FIGS. 31 and 32 show that illumination of IA generates ROS such as singlet oxygen and superoxide. These results indicate that the IA promotes rupture of lysosomes by photosensitization, wherein reactive oxygen species are produced by the IA upon exposure to illumination.

FIGS. 8A-9B show that illumination considerably enhances the cytotoxicity of the IA. FIGS. 9A-9B also show that the enhancement of cytotoxicity is greater in multi-drug resistant cancer cells than in non-resistant cancer cells. FIGS. 10A-11 show that treatment with chloroquine increases the amount of lysosomes in cells, and FIGS. 12A-12C show that treatment with choroquine enhances IA cytotoxicity in the presence of illumination, but not in the absence of illumination. These results indicate that lysosomal rupture by IA photosensitization exhibits a powerful cytotoxic effect, and that this cytotoxic effect is more marked in cells which contain larger numbers of lysosomes, such as multi-drug resistant cells.

FIGS. 30A-30B show that the cytotoxicity of IA upon illumination is associated with destruction of the cytoskeleton.

Figure 24A:
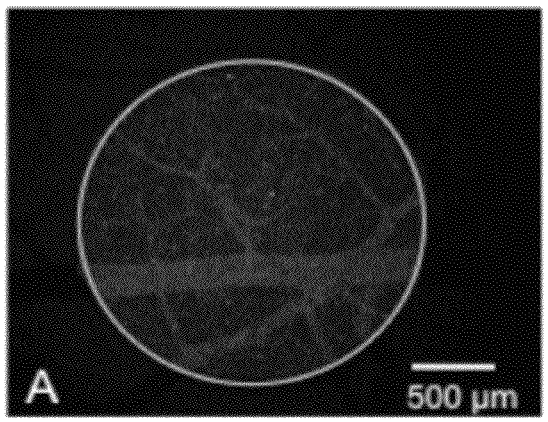
Figure 24B:
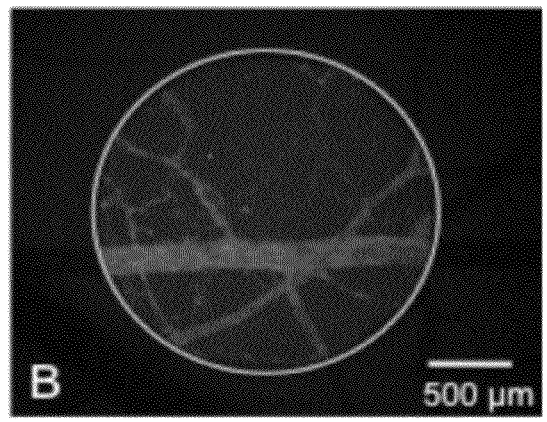
Figure 24C:
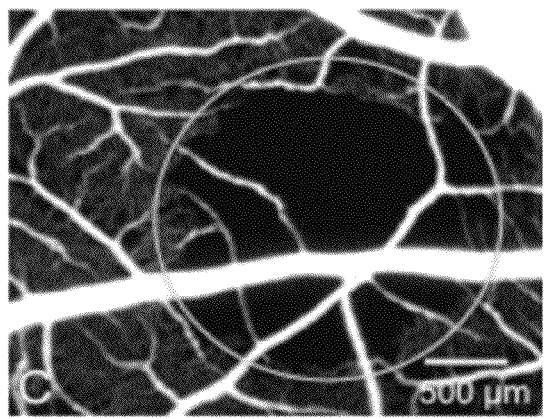
Figure 24D:
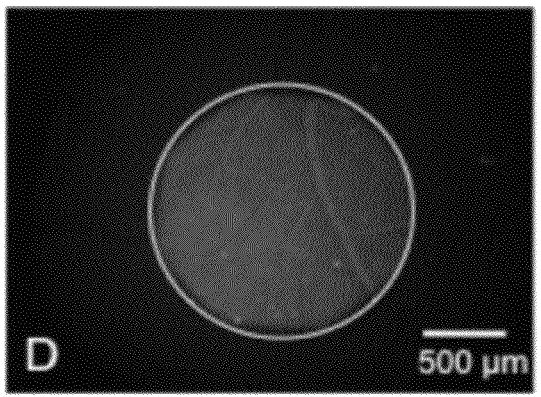
Figure 24E:
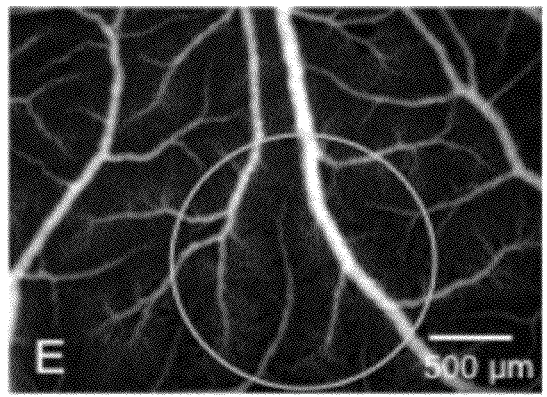

FIG. 17 shows that sunitinib, an additional exemplary chemotherapeutic agent, also accumulates in lysosomes. FIGS. 24A-24C show that doxorubicin, an additional chemotherapeutic agent, accumulates in lysosomes and causes rupture of the lysosomes upon illumination. As sunitinib and doxorubicin are each chromophores and hydrophobic weak bases, these results indicate that a variety of chemotherapeutic agents which are chromophores and hydrophobic weak bases enhance cytotoxicity in a manner similar to that exhibited by IAs.

FIGS. 19A-22B show that photodynamic therapy using an IA as a photosensitizer can be effective at destroying vasculature. FIGS. 23A-27C show that photodynamic therapy using sunitinib as a photosensitizer can be effective at destroying vasculature. FIGS. 28A-29D show that photodynamic therapy using an IA as a photosensitizer can be effective at destroying tumors and their surrounding vasculature.

The above results indicate that a variety of chemotherapeutic agents may be effective as photosensitizers for photodynamic therapy, and therefore useful for treating a proliferative disease or disorder.

According to an aspect of some embodiments of the present invention there is provided a method of treating a proliferative disease or disorder in a subject in need thereof, the method being effected by administering to the subject a chemotherapeutic agent and illuminating a region in a body of the subject which is characterized by the presence of proliferating cells. In some embodiments, the proliferating cells are abnormally proliferating cells.

As used herein, the phrase "chemotherapeutic agent" describes an agent which exhibits a therapeutic anti-proliferative effect in the treatment of a proliferative disease or disorder, for example, a therapeutic cytotoxicity, inhibition of proliferation, and/or inhibition of angiogenesis. However, a compound which exhibits a therapeutic anti-proliferative effect only when acting as a photosensitizer (e.g., when used for photodynamic therapy) is not included within the scope of the phrase "chemotherapeutic agent".

In some embodiments, the chemotherapeutic agent is an agent which has been used in the medical arts to treat a proliferative disease or disorder. For example, the chemotherapeutic agent may be approved by a government agency (e.g., the U.S. Food and Drug Administration and/or the European Medicines Agency) for use in the treatment of one or more proliferative diseases or disorders and/or be undergoing clinical trials for treatment of one or more proliferative diseases or disorders, with the proliferative disease or disorder being as described herein.

Also encompassed within the phrase "chemotherapeutic agent" are compounds which exhibit no or minute anti-proliferative activity when intact, but which exhibit such an activity when exposed to light, via the mechanism of action as described herein.

In some embodiments, the chemotherapeutic agent is a hydrophobic weak base chemotherapeutic agent.

As used herein, the term "weak base" describes a compound which in an aqueous environment exists in an equilibrium between a neutrally charged basic form which is a proton acceptor (also referred to as a "non-protonated" form) and a positively charged conjugate acid form which is a proton donor (also referred to as a "protonated" form). The weak base may optionally exist in equilibrium between more than two forms, for example, having multiple basic forms and/or multiple protonated forms in equilibrium.

In some embodiments, the pKa characterizing the transition between the neutrally charged basic form and its conjugate acid is no more than 14, optionally no more than 13, optionally no more than 12, optionally no more than 11, optionally no more than 10, and optionally no more than 9. In some embodiments, the pKa is at least 4, optionally at least 5, optionally at least 6, and optionally at least 7.

According to optional embodiments, the pKa is in a range of from 5 to 12, optionally from 5.5 to 11, and optionally from 6 to 10.

Thus, the pKa may optionally be lower than a typical physiological pH (e.g., 7-7.5), for example in a range of from 5-7, such that the weak base exists predominantly in a neutrally charged form at the physiological pH, while existing more in a positively charged state at a lysosomal pH level (e.g., 4.5-5.5).

Alternatively, the pKa may be higher than a typical physiological pH, for example in a range of from 7-12, such that the weak base exists predominantly in a positively charged (protonated) form at both a lysosomal pH and at the physiological pH. However, the concentration of the neutrally charged (non-protonated) form will be considerably lower at a lysosomal pH level than at the physiological pH level.

As used herein, the term "hydrophobic" describes a compound which in an octanol-water system dissolves to a greater extent in the octanol, such that the partition coefficient (i.e., the ratio of the concentration of the compound in octanol to the concentration of the compound in water) is more than 1. In other words, logP (i.e., the base-10 logarithm of the ratio) is more than 0.

In some embodiments, logP is at least 0.5, and in some embodiments, logP is at least 1. Optionally, logP is at least 1.5, optionally at least 2, optionally at least 2.5, optionally at least 3, optionally at least 3.5, optionally at least 4, optionally at least 4.5, and optionally at least 5.

As defined herein and in the art, the partition coefficient and logP values refer to partition of a neutrally charged form of a compound in non-ionized water, and the partition coefficient and logP are determined at a pH at which the compound exists substantially as the neutrally charged form. Thus, a weak base described herein is considered hydrophobic when the neutrally charged base form is hydrophobic as defined herein, even if a positively charged conjugate acid form, which may be a predominant form at a physiological pH (e.g., pH 7.4), is not hydrophobic.

In some embodiments, the compound is hydrophobic at a pH of 7.4, such that the compound as a whole (i.e., including all forms of the compound) dissolves to a greater extent in the octanol of an octanol-water system. Thus, the distribution coefficient (i.e., the ratio of the concentration of the compound in all forms in octanol to the concentration of the compound in water) at pH 7.4 is more than 1, and logD (i.e., the base-10 logarithm of the ratio) at pH 7.4 is more than 0.

In some embodiments, logD at pH 7.4 is at least 0.5, optionally at least 1, optionally at least 1.5, optionally at least 2, optionally at least 2.5, and optionally at least 3.

In some embodiments, logP and/or logD are experimentally determined values.

In alternative embodiments, logP and/or logD are calculated according to any suitable technique used in the art, for example, as described in Bram et al. [*Biochem Pharmacol* (2007) 74:41-53].

In some embodiments, the chemotherapeutic agent and the wavelength of the illumination are selected such that the chemotherapeutic agent acts, when exposed to the illumination, as a therapeutically effective photosensitizer.

As used herein, the phrase "photosensitizer" describes a compound which initiates a chemical reaction or a cascade of chemical reactions upon exposure to light (i.e. light characterized by a suitable wavelength), the chemical reaction including formation and/or cleavage of covalent bonds. For example, the photosensitizer may generate a reactive compound and/or free radical upon exposure to light. In exemplary embodiments, the photosensitizer is capable of initiating at least one reactive oxygen species (ROS) (e.g., hydroxyl radical, superoxide, hydrogen peroxide and/or singlet oxygen) upon exposure to light.

In some embodiments, the chemotherapeutic agent acts as a photosensitizer when exposed to illumination at one or more wavelengths in a range of from 400 to 800 nm. Accordingly, the illumination used as described herein is optionally selected such that at least a portion of the illumination is at such a wavelength(s).

The phrase "therapeutically effective photosensitizer" thus describes a photosensitizer which initiates a chemical reaction (e.g., generation of ROS) to a degree (e.g., with respect to an amount of ROS generated) which is sufficiently effective to prevent, alleviate or ameliorate symptoms of disease or prolong the survival of the subject being treated.

The phrase "acts as a therapeutically effective photosensitizer" describes a chemotherapeutic agent, which at a given amount of the agent and at a given wavelength spectrum and dosage of illumination, initiates a chemical reaction to a degree which is sufficiently effective to prevent, alleviate or ameliorate symptoms of disease or prolong the survival of the subject being treated (as described hereinabove).

Optionally, in order to select a chemotherapeutic agent and parameters of illumination (e.g., wavelength spectrum, fluence, irradiance, time of illumination) such that the chemotherapeutic agent acts as a photosensitizer, a cytotoxicity of the chemotherapeutic agent is determined in the presence of such illumination and in the absence thereof (e.g., in the dark), wherein enhancement of the cytotoxicity by the illumination is considered proof that the chemotherapeutic agent acts as a photosensitizer. When a chemotherapeutic agent is found to act as a photosensitizer, an amount of the chemotherapeutic agent which provides a therapeutically effective photosensitizer (as defined herein) can then be readily determined.

In some embodiments, a cytotoxicity is determined by measuring an $IC_{50}$ value for the chemotherapeutic agent in an acceptable in vitro cell viability assay (i.e., a concentration of chemotherapeutic agent at which cell viability is 50% of normal), for example, an XTT assay (as exemplified herein). As is well known in the art, XTT selectively stains viable cells, such that cell viability may be readily determined as a percentage of light absorption by XTT, as compared to control cells. As exemplified herein, by measuring cell viability at a range of concentrations of the chemotherapeutic agent, the $IC_{50}$ may be readily determined.

The cell viability assay is preferably performed using cells which are similar to the proliferating cells which are a target of the treatment. For example, the assay may be performed using cells of the tissue type which is the same or similar to a tissue type of the targeted proliferating cells. Similarly, if the targeted proliferating cells are known (e.g., following a biopsy) to be multi-drug resistant or non-resistant, the cells for the assay are optionally selected accordingly.

In some embodiments, the selected chemotherapeutic agent and the parameters of illumination are characterized in that an $IC_{50}$ value of the agent when exposed to the illumination is no more than 50% (i.e., reduced at least two-fold), and optionally no more than 20% (i.e., reduced at least 5-fold), of the $IC_{50}$ value in the absence of illumination. In some embodiments, the $IC_{50}$ when exposed to the illumination is no more than 10% (i.e., reduced at least 10-fold), optionally no more than 3%, optionally no more than 1%, optionally no more than 0.3%, and optionally no more than 0.1%, of the $IC_{50}$ in the absence of illumination.

Without being bound by any particular theory it is believed that utilizing a chemotherapeutic agent as a photosensitizer is particularly effective, as a therapeutic effect may be obtained from both the light-dependent photosensitization activity thereof and from a light-independent therapeutic anti-proliferative effect thereof. Hence, a synergistic combination of anti-proliferative activities may be obtained.

According to optional embodiments of the present invention, the chemotherapeutic agent is capable of accumulating within lysosomes of at least a portion of the proliferating cells which are to be subjected to illumination (e.g., as described herein). As discussed hereinabove and exemplified in the Examples section below, a photosensitization activity of a chemotherapeutic agent accumulated within lysosomes can lead to photodestruction of lysosomes.

Without being bound by any particular theory, it is believed that photodestruction of lysosomes results in severe damage to cells due to release of the acidic content and hydrolytic enzymes of the lysosomes into the cytosol and/or to the disruption of vital cellular functions of the lysosomes. It is further believed that release of a chemotherapeutic agent from the lysosomes facilitates the cytotoxic effect of a chemotherapeutic agent which targets a different part of the cell (e.g., the nucleus). For example, as exemplified herein, photodestruction of lysosomes facilitates entry of IAs and doxorubicin to the nucleus, where these agents are known in the art to exert a cytotoxic effect. Thus, the photosensitization activity of the chemotherapeutic agent can synergistically enhance the light-independent cytotoxic effect of the chemotherapeutic agent.

In exemplary embodiments, no photosensitizer is used other than a chemotherapeutic agent as described herein.

In alternative embodiments, an additional photosensitizer (e.g., a photosensitizer which is used in the medical arts for photodynamic therapy) is used in combination with the chemotherapeutic agent described herein.

Herein, the phrase "proliferative disease or disorder" refers to a disease or disorder associated with hyperplasia, benign or malignant neoplastic cell growth (including cancer) and/or with neovasculature formation and/or angiogenesis (e.g., age-related macular degeneration).

Exemplary proliferative disease or disorders treatable as described herein include, but are not limited to, cancer and hyperplasia.

According to some embodiments of the invention, the cancer is a multi-drug resistant cancer.

As exemplified herein, the methodologies described herein are particularly effective at killing multi-drug resistant cancer cells. Consequently, upon illumination, a cytotoxicity of the chemotherapeutic agent towards multidrug-resistant may be almost as great as, as great as, and even greater than, a cytotoxicity of the agent towards non-resistant cells, although in the absence of illumination the cytotoxicity of the agent is typically far greater for non-resistant cells than for resistant cells. Thus, the use of illumination in combination with the chemotherapeutic agent, as described herein, partially or even completely overcomes the multi-drug resistance.

Without being bound by any particular theory, it is believed that multi-drug resistant cells are specifically susceptible to the lysosome-mediated cytotoxic mechanism described herein because these cells contain unusually large amounts of lysosomes. The specific relative susceptibility of these cells to a lysosome-mediated cytotoxic mechanism thus partially or completely overcomes the general resistance of these cells to chemotherapeutic agents. In addition, it is further believed that accumulation of a chemotherapeutic agent in lysosomes, as described herein, may also counteract the multi-drug resistance by at least partially protecting the agent prior to illumination from being exported from the cell via an efflux mechanism characteristic of multi-drug resistant cells, while the agent remains available for exerting a cytotoxic effect upon illumination, as described herein.

In some embodiments, the chemotherapeutic agent is administered at a dosage which, by itself (i.e., in the absence of illumination), is sufficient to produce a therapeutic effect, i.e., to prevent, alleviate or ameliorate symptoms of a proliferative disease or disorder or prolong the survival of the subject being treated.

Herein, a minimal dosage of a chemotherapeutic agent sufficient to produce a therapeutic effect in the absence of light is referred to as a "cytotoxic dosage". The cytotoxic dosage of an agent may vary according to the disease or disorder being treated. A cytotoxic dosage may be, for example, a minimum effective dose (MED). MED values for chemotherapeutic agents used in the medical arts will be available to the practitioner.

In alternative embodiments, the chemotherapeutic agent is administered at a dosage which is less than a cytotoxic dosage of the agent. The reduced dosage may be desirable in order to reduce deleterious side effects of the chemotherapeutic agent, because the light-independent cytotoxicity of the agent may be enhanced by photodestruction of lysosomes (as described herein), and/or because a strong light-independent cytotoxic effect may be unnecessary in view of the light-dependent cytotoxicity of the agent. In some embodiments, the agent is administered at a dosage of no more than 50% of the cytotoxic dosage. In some embodiments, the administered dosage is no more than 20%, and optionally no more than 10%, of the cytotoxic dosage.

In some embodiments, the region of the body which is illuminated comprises a tumor. The tumor may be a benign tumor (e.g., a mole, a papilloma, a lipoma, a chondroma, an adenoma, a neoplasm) or a malignant tumor (a cancerous tumor). Tumors are generally easier to treat via illumination than are other forms of cell proliferation, as the proliferating cells are relatively co-localized. In some embodiments, the tumor is present at a surface of the body (e.g., in the skin) and/or is less than 10 mm thick (optionally less than 5 mm, and optionally less than 2.5 mm thick), which further facilitates illumination of the proliferating cells.

According to optional embodiments, the fluence (energy per area) of the illumination is in a range of from 2 to 1000 $J/cm^2$, optionally at least 10 $J/cm^2$, and optionally at least 20 $J/cm^2$. In some embodiments, the fluence is in a range of from 10 to 300 $J/cm^2$, and optionally from 20 to 200 $J/cm^2$.

The parameters of illumination are optionally selected so as to avoid excessive heating of a tissue being illuminated, i.e., heating which may harm the subject and/or interfere with a therapeutic effect of the treatment. Optionally, the illumination increases a temperature of the illuminated tissue by less than 10° C., optionally by less than 4° C., optionally by less than 2° C., and optionally by less than 1° C.

It is to be appreciated that for any selected fluence of illumination, a degree of heating may be reduced by using a lower irradiance (power per area) for a longer time of illumination.

It is to be further appreciated that a degree of heating will be minimized by using wavelengths which are minimally absorbed by tissue. The use of such wavelengths may also advantageously increase the percentage of light which will be available to activate the chemotherapeutic agent.

The absorption spectrum of most tissues is relatively similar to that of hemoglobin, in which absorption is relatively strong at wavelengths below about 430 nm or in a range of about 530 nm to about 580 nm, and particularly strong at wavelengths of less than about 420 nm. Hence, the chemotherapeutic agent and illumination wavelength(s) are optionally selected such that photoactivation of the chemotherapeutic agent is at a wavelength of at least 420 nm, optionally at least 430 nm, and optionally outside of a range of 530-580 nm.

In addition, longer wavelengths undergo less scattering and less absorption by melanin, and hence generally penetrate deeper (particularly when illuminating skin). Hence, in some embodiments, photoactivation of the chemotherapeutic agent is at a relatively long wavelength (e.g., at least 450 nm, at least 500 nm, at least 550 nm, at least 600 nm), for example, when illuminating skin, particularly in a dark-skinned subject, and/ or when the region to be illuminated is at least 1 mm thick (e.g., at least 2 mm thick, at least 4 mm thick, at least 8 mm thick).

If the region to be illuminated is not at or close to a surface of the body, the region may be illuminated, for example, by using surgery to expose the region to be illuminated, and/or using endoscopy to direct the light to the region.

The chemotherapeutic agent may be administered locally (e.g., by topical administration, by local injection) to the region to be illuminated, or administered systemically. Systemic administration can be effected, for example, via a transdermal, transmucosal, oral, buccal, inhalation, parenteral and/or rectal route.

In exemplary embodiments, the agent is administered by intravenous injection or by topical administration.

Surgery (including keyhole surgery) may optionally be used to facilitate administration, especially local administration (e.g., by topical administration, by local injection) of the chemotherapeutic agent directly to a region to be illuminated.

According to another aspect of embodiments of the invention, there is provided a hydrophobic weak base chemotherapeutic agent such as is described herein, for use in the treatment of a proliferative disease or disorder in a subject in need thereof in combination with illumination of a region of a body of the subject which is characterized by the presence of proliferating cells (e.g., as described herein). The treatment is preferably effected as described herein. In some embodiments, the agent is an imidazoacridinone as described herein. In some embodiments, the agent is a receptor tyrosine kinase inhibitor as described herein.

According to another aspect of embodiments of the invention, there is provided a use of a hydrophobic weak base chemotherapeutic agent such as is described herein, in the manufacture of a medicament for the treatment of a proliferative disease or disorder in a subject in need thereof (e.g., as described herein). The medicament is identified for use in combination with illumination of a region in a body of the subject which is characterized by the presence of proliferating cells (e.g., as described herein). Optionally, the medicament is identified for use in accordance with a method described herein. In some embodiments, the agent is an imidazoacridinone as described herein. In some embodiments, the agent is a receptor tyrosine kinase inhibitor as described herein.

In any of the methods and uses described herein, the chemotherapeutic agent can be used either per se, or as a part of a pharmaceutical composition which further comprises a pharmaceutically acceptable carrier, as defined herein.

Chemotherapeutic agents which are suitable for use in the context of embodiments of the invention include, without limitation, imidazoacridinone agents, receptor kinase inhibitors, actinomycin agents (e.g., actinomycin D, 7-aminoactinomycin D), camptothecin and derivatives thereof (e.g., topotecan, irinotecan, exatecan, lurtotecan, DB-67, BNP-1350, ST-1481, and CKD602), and anthracenedione agents (e.g., mitoxantrone, pixantrone, ametantrone and piroxantrone). However, it is to be appreciated that other chemotherapeutic agents may be suitable for use in the context of embodiments of the invention. In some embodiments, the chemotherapeutic agent is not an anthracenedione.

According to some embodiments, the chemotherapeutic agent is an imidazoacridinone chemotherapeutic agent. Suitable imidazoacridinones include, without limitation, imidazoacridinone compounds having the general formula:

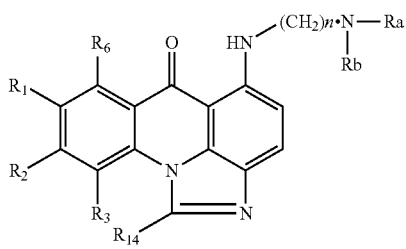

wherein:

$R_1$, $R_2$, $R_3$, $R_6$ and $R_{14}$ (the nomenclature of these substituents is standard for IAs) is are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl;

Ra and Rb are each independently selected from the group consisting of hydrogen, alkyl, alkenyl, alkynyl, cycloalkyl, heteroalicyclic, aryl, and heteroaryl; and n is from 1 to 30.

In some embodiments, $R_1$, $R_2$, $R_3$, $R_6$ and $R_{14}$ are each independently selected from the group consisting of hydrogen, hydroxy, alkoxy and alkyl. Optionally, the alkoxy and/or alkyl substituents comprise 1 to 4 carbon atoms, optionally 1 or 2 carbon atoms, and optionally 1 carbon atom (i.e., the alkoxy is methoxy and/or the alkyl is methyl).

In some embodiments, $R_1$ is hydroxy or alkoxy (optionally methoxy).

In some embodiments, $R_{14}$ is hydrogen or alkyl (optionally methyl).

In some embodiments, n is in a range of from 2 to 10, optionally from 2 to 6, and optionally from 2 to 4. In exemplary embodiments, n is 2 or 3.

In some embodiments, at least one of Ra and Rb is alkyl, and in some embodiments, Ra and Rb are each alkyl, optionally the same alkyl. Optionally, Ra and/or Rb is an alkyl comprising 1 to 4 carbon atoms. In exemplary embodiments, Ra and Rb are selected from among methyl and ethyl.

In exemplary embodiments, $R_2$, $R_3$ and $R_6$ are each hydrogen.

In some embodiments, the imidazoacridinone is such that exhibits a resistance to ABCG2-dependent efflux.

As previously described, resistance to efflux is obtained by selecting a compound wherein none of $R_1$, $R_2$ and $R_3$ is hydroxy.

Alternatively or additionally, resistance to efflux is obtained by selecting a compound in which the variables n, Ra and/or Rb are such that the compound is characterized by a relatively long distal aliphatic side chain. In some embodiments, the n is greater than 5, optionally greater than 6. In some embodiments, Ra and Rb together comprise more than 5 carbon atoms.

According to optional embodiments, the chemotherapeutic agent is a receptor tyrosine kinase inhibitor.

As exemplified in the Examples section that follows, it has been surprisingly uncovered that an exemplary receptor tyrosine kinase inhibitor, sunitinib, which was known as an anti-angiogenesis agent, accumulates in lysosomes of treated cells.

Suitable receptor tyrosine kinase inhibitors include, without limitation, pyrrole substituted 2-indolinone compounds, for example, compounds having the general formula:

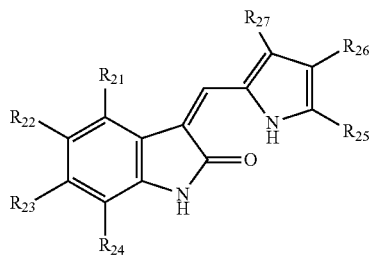

wherein:

$R_{21}$-$R_{27}$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl.

Examples of such receptor tyrosine kinase inhibitors include sunitinib and toceranib.

In some embodiments, $R_{25}$ and $R_{27}$ are each alkyl, optionally an alkyl of 1 to 4 carbon atoms, optionally 1 or 2 carbon atoms, and optionally 1 carbon atom (i.e., methyl).

In some embodiments, $R_{22}$ is halide. Fluoro is an exemplary halide.

In some embodiments, $R_{21}$, $R_{23}$ and $R_{24}$ are each hydrogen.

In some embodiments, $R_{26}$ is an amide group. In some embodiments, the amide group is —C(=O)NH—$R_{28}$, wherein $R_{28}$ is an amino substituted alkyl. Optionally, the amino substituted alkyl is ethyl substituted at the 2-position by an amine group, optionally a dialkylamino group.

According to some embodiments, the chemotherapeutic agent is a camptothecin.

Herein, the phrase "a camptothecin" encompasses the compound known in the art as camptothecin (e.g., as depicted below), as well as derivatives thereof, such as substituted camptothecin (e.g., camptothecin substituted with a substituent described herein).

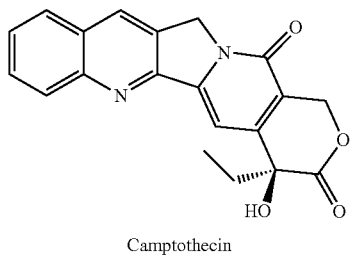 [SMILES: CC[C@@]1(O)C(=O)OCc2c1cc1n(c2=O)Cc2cc3ccccc3nc2-1]

Camptothecin

In some embodiments, the quinoline moiety of camptothecin is substituted at one or more positions thereof. In some embodiments, one or more substituent is selected from the group consisting of hydroxy, halo (e.g., fluoro), non-substituted alkyl (e.g., methyl, ethyl), substituted alkyl (e.g., an aminoalkyl, for example, dimethylaminomethyl, isopropylaminoethyl, (4-methylpiperazinyl)methyl), silyl (e.g., alkylsilyl), carboxy, and alkoxy. Alternatively or additionally, any substituent described herein may be attached to the camptothecin structure depicted hereinabove (e.g., to the quinoline moiety thereof). In some embodiments, one or more substituent is attached at two positions on the camptothecin, thereby forming a ring (e.g., as in the structures of lurtotecan and exatecan).

As used herein, the terms "amine" and "amino" refer to a —NR'R" group, wherein R' and R" are selected from the group consisting of hydrogen, alkyl, cycloalkyl, heteroalicyclic (bonded through a ring carbon), aryl and heteroaryl (bonded through a ring carbon). Optionally, R' and R" are selected from the group consisting of hydrogen and alkyl comprising 1 to 4 carbon atoms. In some embodiments, R' and R" are hydrogen.

A "dialkylamino" group is an amino group wherein both R' and R" are alkyl. The dialkylamino group may comprise two separate alkyl groups (e.g., a diethylamino group such as is present in sunitinib) or the two alkyl groups may form a ring (e.g., a pyrrole ring such as is present in toceranib).

As used herein throughout, the term "alkyl" refers to a saturated aliphatic hydrocarbon including straight chain and branched chain groups. Preferably, the alkyl group has 1 to 20 carbon atoms. Whenever a numerical range, e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, 0-thiocarbamyl, N-thiocarbamyl, C-amido, N-amido, C-carboxy, O-carboxy, sulfonamido, and amino, as these terms are defined herein.

An "alkenyl" group refers to an unsaturated aliphatic hydrocarbon which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or unsubstituted. When substituted, the substituent group can be, for example, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "alkynyl" group refers to an unsaturated aliphatic hydrocarbon which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or unsubstituted. When substituted, the substituent group can be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthyl and anthracenyl. The aryl group may be substituted or non-substituted. When an aryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazine, pyrazole, pyridine, pyrimidine, quinoline, isoquinoline and purine. The heteroaryl group may be substituted or non-substituted. When a heteroaryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. It is to be appreciated that a substituent (e.g., oxo) may be a component of the conjugated pi-electron system.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropyl, cyclobutyl, cyclopentyl, cyclopentenyl, cyclohexyl, cyclohexadiene, cycloheptyl, cycloheptatrienyl, norbornyl and adamantyl. A cycloalkyl group may be substituted or non-substituted. When a cycloalkyl is substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thio-carbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A "carbonyl" group refers to a —C(=O)—R' group, where R' is defined as hereinabove.

A "thiocarbonyl" group refers to a —C(=S)—R' group, where R' is as defined herein.

A "carboxy" group encompasses C-carboxy and O-carboxy groups, as defined herein.

A "C-carboxy" group refers to a —C(=O)—O—R' group, where R' is as defined herein.

An "O-carboxy" group refers to an R'C(=O)—O— group, where R' is as defined herein.

A "thiocarboxy" or "thiocarboxylate" group refers to both —C(=S)—O—R' and —O—C(=S)R' groups.

A "sulfonate" group refers to both —S(=O)$_2$—O—R' and —O—S(=O)$_2$—R' groups, where R' is as defined herein.

A "halide" or "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl"" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses 0-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

A "nitro" group refers to an —NO$_2$ group.

A "nitroso" group refers to an —NO group.

A "nitrile" or "cyano" group refers to a —C≡N group.

An "isonitrile" group refers to a —N≡C group

An "oxo" group refers to a =O group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

A "urea" group refers to an —N(R')—C(=O)—NR"R'" group, where each of R' and R" is as defined herein, and R'" is defined as R' and R" are defined herein.

The term "thiourea" describes a —N(R')—C(=S)—NR"— group, with each of R' and R" as defined hereinabove.

As used herein, the term "epoxide" describes a

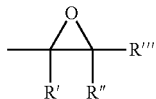

group, where R', R" and R'" are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, R"", wherein R"" is defined according to the same definition as R'.

The term "hydrazine", as used herein, describes a —NR'—NR"R'" group, with R', R" and R'" as defined herein.

As exemplified in the Examples section, increasing an amount of lysosomes in target cells (by administration of chloroquine) increases a susceptibility of cells to illumination.

Hence, according to optional embodiments of any of the aspects of the invention described herein, the chemotherapeutic agent may be administered in combination with an additional agent, which is capable of increasing an amount of lysosomes in cells, for example, chloroquine.

The additional agent may be administered via any route described herein.

The additional agent may be administered prior to administration of the chemotherapeutic agent, subsequently to administration of the chemotherapeutic agent (but prior to illumination), and/or concomitantly with administration of the chemotherapeutic agent.

According to another aspect of embodiments of the invention, there is provided a pharmaceutical composition comprising a therapeutically effective amount of a chemotherapeutic agent which acts as a photosensitizer as described herein, a therapeutically effective amount of an additional agent as described herein (e.g., chloroquine), and a pharmaceutically acceptable carrier.

As used herein a "pharmaceutical composition" refers to a preparation of one or more of each of the chemotherapeutic agent and additional agent described hereinabove, with other chemical components such as pharmaceutically acceptable and suitable carriers and excipients. The purpose of a pharmaceutical composition is to facilitate administration of compounds to an organism.

Hereinafter, the term "pharmaceutically acceptable carrier" refers to a carrier or a diluent that does not cause significant irritation to an organism and does not abrogate the biological activity and properties of the administered compound(s). Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention thus may be formulated in conventional manner using one or more pharmaceutically acceptable carriers comprising excipients and auxiliaries, which facilitate processing of the active ingredients (e.g., chemotherapeutic agent and additional agent) described herein into preparations which can be used pharmaceutically. Proper formulation is dependent upon the route of administration chosen.

For injection, the active ingredients may be formulated as aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the active ingredients can be formulated readily by combining the active ingredients with pharmaceutically acceptable carriers well known in the art. Such carriers enable the active ingredients described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of doses of an active ingredients.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredients and a suitable powder base such as, but not limited to, lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredient preparation in water-soluble form. Additionally, suspensions of the active ingredients may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, active ingredients may be in powder form for constitution with a suitable vehicle, e.g., sterile, pyrogen-free water, before use.

The active ingredients described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a "therapeutically effective amount" means an amount of an ingredient effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any chemotherapeutic agent used in embodiments of the invention, either alone or in combination with an additional agent such as chloroquine, the therapeutically effective amount or dose can be estimated initially from activity assays in animals. For example, a dose can be formulated in animal models to achieve a circulating concentration range that includes the $IC_{50}$ in the presence of illumination, as determined by cell viability assays. Such information can be used to more accurately determine useful doses in humans.

Toxicity and therapeutic efficacy of the active ingredients described herein can be determined by standard pharmaceutical procedures in experimental animals, e.g., by determining the $LD_{50}$ (lethal dose causing death in 50% of the tested animals) for a subject active ingredient of combination of active ingredients. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active ingredients which are sufficient to maintain the desired effects. Such plasma levels will vary for each preparation, but can be estimated for any given parameters of illumination from in vitro data, e.g., according to $IC_{50}$ values from cell viability assays. Dosages necessary to achieve a sufficient plasma level will depend on individual characteristics and route of administration. HPLC assays or bioassays can be used to determine plasma concentrations.

The amount of a composition to be administered will, of course, be dependent on the subject being treated, the severity of the affliction, the manner of administration, the judgment of the prescribing physician, etc.

Compositions of embodiments of the present invention may, if desired, be presented in a pack or dispenser device, such as an FDA (the U.S. Food and Drug Administration) approved kit, which may contain one or more unit dosage forms containing the active ingredients. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising active ingredients described herein formulated in a compatible pharmaceutical carrier may also be prepared, placed in an appropriate container, and labeled for treatment of an indicated disease or disorder, as is detailed hereinabove.

Thus, according to an embodiment of the present invention, the pharmaceutical compositions described herein are packaged in a packaging material and identified in print, in or on the packaging material, for use in the treatment of a disease or disorder in combination with illumination, as described herein.

It is expected that during the life of a patent maturing from this application many relevant hydrophobic weak base chemotherapeutic agents as described herein will be developed and the scope of the term "chemotherapeutic agent" is intended to include all such new technologies a priori.

As used herein the term "about" refers to ±5%.

The terms "comprises", "comprising", "includes", "including", "having" and their conjugates mean "including but not limited to".

The term "consisting of means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:
Acridine orange was obtained from Sigma-Aldrich;
ammonium chloride was obtained from Sigma-Aldrich;
Bafilomycin A1 was obtained from Enzo Life Sciences;
C-1311, C-1330, C-1375 and C-1379 were synthesized by Dr. M. Cholody, Dr. B. Horowska and Dr. M. Konieczny at the Dept. of Pharmacological Technology and Biochemistry, Gdansk University of Technology, Poland;
chloroquine was obtained from Sigma-Aldrich;
crystal violet was obtained from Sigma-Aldrich;
5,5-dimethyl-1-pyrroline-N-oxide (DMPO) was obtained from Sigma-Aldrich;
dimethyl sulfoxide was obtained from Sigma-Aldrich;
dimethyl urea was obtained from Sigma-Aldrich;
fluorescein isothiocyanate-dextran was obtained from Sigma-Aldrich;
L-histidine was obtained from Sigma-Aldrich;
LysoTracker® Red DND99 was obtained from Invitrogene;
MitoTracker® Red CMXRos was obtained from Invitrogene;
RPMI-1640 medium was obtained from Gibco;
sodium azide was obtained from Sigma-Aldrich.

Cancer Cell Cultures:
Human non-small cell lung cancer A549 cells and their ABCG2-overexpressing MDR (multi-drug resistant) A549/K1.5 sub-line; ovarian carcinoma cell line 2008 and its stable MRP1-transfectant 2008/MRP1; and human non-small lung cancer cell line SW1573 and its ABCB1-overexpressing subline SW1573/2R160) were maintained in RPMI-1640 medium supplemented with 10% fetal bovine serum, 2 mM glutamine, 100 µg/ml penicillin and streptomycin (Biological Industries, Beth-Haemek, Israel) in a humid atmosphere containing 5% $CO_2$ at 37° C.

A549/K1.5 and SW1573/2R160 cells were continuously grown in selective medium containing 1.5 µM C1305 (as described in Bram et al. [*Biochem Pharmacol* 2007, 74:41-53]) or 100 nM doxorubicin, respectively. Cells were grown in drug-free conditions for one week before any analysis.

Cytotoxicity Assays:
Parental cells and their MDR (multi-drug resistant) sublines were seeded in 96-well plates ($2\times10^4$ cells/well in 90 µl growth medium/well). After 24 hours of incubation, cells were exposed to various concentrations of the tested cytotoxic drug (e.g., the imidazoacridinones (IAs) C-1330, C-1375 and C-1379). Following incubation for 2 hours, the drug-containing medium was replaced by drug-free medium. The cells were then placed on an illuminator plate (Model 460, thin line series, S&S X-Ray Products Inc., Brooklyn, N.Y.) for 1 hour, thereby achieving a light dose of 5 $J/cm^2$ white light. After illumination, plates were further incubated for an additional 24 hours.

Cell viability was determined using an XTT (2,3-bis-(2-methoxy-4-nitro-5-sulfophenyl)-2H-tetrazolium-5-carboxanilide) Cell Proliferation Kit (Biological Industries). The drug concentrations required to inhibit cell growth by 50% (i.e., $IC_{50}$ values) were determined from the cell survival curves in the absence and in the presence of illumination. Results are presented as mean values of at least three independent experiments.

Live Cell Fluorescent Imaging:

Parental A549 and MDR (multi-drug resistant) A549/K1.5 cells were seeded in 35 mm glass-bottom dishes (FluoroDish, World Precision Instruments) and allowed to grow for at least 24 hours.

Lysosomes and mitochondria were stained by incubating the cells 100 nM LysoTracker® Red or 100 nM MitoTracker® Red, respectively, for 1 hour. For subcellular localization of C-1330, cells were also stained with 10 µM C-1330 for 30 minutes.

Nuclear staining was performed prior to fluorescence imaging by replacing the growth medium with medium containing 2 µg/ml Hoechst 33342, followed by incubation for 10 minutes. Prior to nuclear staining, A549/K1.5 cells were incubated for 1 hour with 10 µM fumitremorgin C (FTC) to prevent efflux of Hoechst 33342 by ABCG2.

Live cell fluorescent imaging was performed using an Axiovert 200 inverted fluorescence microscope (Carl Zeiss) equipped with a digital camera. In order to visualize C-1330 or doxorubicin, cells were illuminated with blue light using a GFP+DsRed filter (excitation wavelength 470±27 nm; emission wavelength 512±20 nm and 630±98 nm. Light intensity in the illuminated cell monolayer zone was approximately 3 $W/m^2$, and 30 seconds of illumination resulted in a dose of approximately 90 $J/m^2$. LysoTracker® Red DND-99 and MitoTracker® Red were visualized using a Cye3 red filter (excitation wavelength 545±25 nm; emission wavelength 605±70 nm), whereas a DAPI filter (excitation wavelength 365 nm; emission wavelength 445±50 nm) was used to observe viable nuclear DNA staining with Hoechst 33342. Light intensity was maintained at 12.5% of the maximum. The magnification used was ×630.

Crystal Violet Staining:

A549 and A549/K1.5 cells were grown to full confluence on glass-bottom plates and loaded with 10 µM C-1330 for 30 minutes. Before illumination, the spent medium was replaced by fresh medium. Using the inverted fluorescence microscope as a source of illumination, each plate was illuminated for 1 minute at a wavelength of 470 nm, at an intensity of approximately 3 $W/m^2$. Cells were then incubated at 37° C. for an additional 48 hours. The cells were then washed twice with PBS, fixed with 70% methanol for 10 minutes and stained with a diluted dye solution (1:5) of crystal violet. Stained monolayer cells were then washed three times with double distilled water. Crystal violet-stained cells were then examined and photographed using an M80 binocular at a ×8 magnification (Leica Microsystems GmbH), and by an inverted Cell-Observer microscope, at a ×1000 magnification (Carl Zeiss).

Endothelial Cell Cultures:

Human umbilical vein endothelial cells (HUVEC) were isolated by perfusion of umbilical veins (Department of Obstetrics and Gynaecology, VU University Medical Center) with trypsin. Cells were routinely cultured in RPMI-1640 medium (Life Technologies, Breda, The Netherlands) supplemented with 10% heat-inactivated human serum, 10% heat-inactivated FCS, 2 mM L-glutamine (Life Technologies, Netherlands), 50 mg/ml streptomycin and 50 U/ml penicillin (ICN Biomedicals) in a 0.2% gelatin coated 75 $cm^2$ tissue culture flask at 37° C. in an atmosphere with 5% $CO_2$.

HUVEC used for experiments were cultured without addition of extra growth factors and used for experiments between passage 2 and 4.

Endothelial cell lines RF24 and HMEC, were provided by Dr. H. Pannekoek (CLB, Amsterdam, Netherlands) and Dr. D van der Schaft (Maastricht University), respectively.

Measurement of Imidazoacridinone and Sunitinib Spectra:

Stock solutions containing sunitinib or the imidazoacridinones (IAs) C-1375 and C-1379 in 100% dimethyl sulfoxide were diluted with aqueous 0.9% NaCl solution under continuous stirring. Absorption spectra were recorded with a two-beam Cary 500 UV-VIS-NIR spectrophotometer (Varian) in 1 cm long Suprasil® quartz cuvettes (Hellma), at an average scan speed of 600 nm/minute, at 20° C. The steady state emission and excitation spectra were recorded with an LS 50B luminescence spectrometer (Perkin-Elmer).

Chorioallantoic Membrane (CAM) Model of Photodynamic Therapy:

Fertilized chicken eggs (Animalco AG) were labeled and transferred into a hatching incubator with a relative air humidity of 65% and a temperature of 37° C. The incubator was equipped with an automatic fan (Savimat). On embryonic development day (EDD) 3, a hole of approximately 3 mm in diameter was opened in the eggshell above the air pouch of the egg and covered with Parafilm® wrapping film (Pechiney) to prevent dehydration and possible infections. The eggs were then returned to the incubator in a static position until use. On EDD 11, the hole in the shell was extended to a diameter of approximately 3 cm in order to provide better access to the chorioallantoic membrane (CAM) during experiments.

Eggs were placed under an Eclipse 600 FN epi-fluorescence microscope equipped with a Plan Apo 4/0.2, working distance 20 objective (Nikon). Microscopic observation and illumination of a region of the CAM was performed as described previously [Lim et al., *Photochem Photobiol* 2010, 86:397-402; Lim et al., *J Med Chem* 2010, 53:2865-2874; Nowak-Sliwinska et al., *Angiogenesis* 2010, 13:281-292]. Illumination was provided by a 100 W high pressure Hg-arc lamp. Light doses were adjusted with neutral density filters and measured with a calibrated Field-Master GS power meter (Coherent Inc.). Fluorescence images were acquired with an F-view II 12-bit monochrome Peltier-cooled digital CCD camera driven with analySIS DOCU software (Soft Imaging System GmbH).

For excitation and detection of imidazoacridinones (IAs) or sunitinib, the microscope was equipped with a filter set (Nikon) characterized by excitation wavelengths of 420±20 nm and emission wavelengths of >470 nm, After the treatment the eggs were numbered, covered and returned to the incubator. Each treatment group included 5 eggs.

Fluorescein Isothiocyanate (FITC)-Dextran Fluorescence Angiography:

Chorioallantoic membranes (CAMs) were intravenously injecting chorioallantoic membranes with 20 µl of a solution of FITC-dextran (20 kDa, 25 mg/ml). Fluorescence angiography was then performed using light from an Hg-arc lamp and light filters (Nikon) which provided excitation wavelengths of 470±20 nm and emission wavelengths of >520 nm for observing the fluorescence. In order to increase the quality of the recorded angiographs, a light absorber, in the form of India ink, was injected (30 µl) into the extra-embryonic cavity. The purpose of this second injection was to decrease the influence of the CAM auto-fluorescence background, which changes rapidly with time due to the embryo's movement. The India ink was filtered shortly before injection, using a sterile cellulose acetate membrane with 0.2 µm pores (Renner GmbH).

Texas Red-Phalloidin Staining:

A549 cells were grown on coverslips in 24-well plates until confluence was reached. Cells were then incubated with 10 μM C-1330 for 30 minutes and then exposed to light for 1 minute, in order to achieve lysosomal photodestruction. Control cells were loaded with C-1330 but were not illuminated. C1330-loaded cells were ether fixed and stained with Texas Red®-X Phalloidin (Life Technologies) with no illumination or stained with Texas Red®-X Phalloidin 2 hours after illumination. Cells were then washed twice with PBS and fixed by adding 4% formaldehyde for 10 minutes at room temperature. Following two additional washes with PBS, 0.1% Triton X-100 was added for 10 minutes, and then washed twice to remove the Triton X-100. Blocking was then achieved using a solution of 20% skim milk and 2.5% fetal calf serum for 20 minutes. At this stage, 5 μl of Texas Red®-X Phalloidin stock solution was added to 0.2 ml of PBS and the samples were incubated for 20 minutes while being protected from light. The samples were finally rinsed to remove excess Texas Red®-X Phalloidin. Coverslips were removed gently from wells and attached onto slides using Fluoromount-G. Fluorescent cells were analyzed by a fluorescence microscope, using an excitation wavelength of 545 nm and an emission wavelength of 605 nm.

Detection of Superoxide and Singlet Oxygen:

Superoxide radical anion was detected by electron paramagnetic resonance (EPR) spin trapping using 5,5-dimethyl-1-pyrroline-N-oxide (DMPO) as a spin trap, according to procedures as described by Panzella et al. [*Photochem Photobiol* 2010, 86:757-764] and Zareba et al. [*Photochem Photobiol* 2006, 82:1024-1029]. IA solutions containing 0.1 M DMPO in a DMSO/$H_2O$ (9:1) medium were illuminated in a 0.25 mm quartz cell within the resonant cavity of a Bruker EMEX-AA EPR spectrometer (Bruker BioSpin, Germany) with 400-490 nm light derived from a Cermax PE300CE-13FM 300 W lamp in an air-cooled housing (Perkin Elmer). This light source was equipped with the necessary combination of cut-off and band-pass filters. Relative yields of the photo-formation of superoxide anion by IAs were determined in the presence or absence of NADH, used as an auxiliary electron donor, by comparing rates of the accumulation of the DMPO-superoxide adduct (DMPO—OOH) for IAs and for riboflavin (with and without EDTA).

Quantum yields for singlet oxygen generation upon illumination of IAs were determined relative to that of Rose Bengal (RB) by measuring time-resolved luminescence intensity at 1270 nm in DMSO or acetonitrile solutions, after excitation of the tested compounds or RB at 355 nm with microjoule 750 picoseconds pulses generated by a microchip Nd:YAG laser (Pulselas-P-1064-FC, Alphalas GmbH, Germany) operating with 2-10 kHz repetition rate. Near-infrared luminescence was measured perpendicularly to the excitation beam in a photon-counting mode, as described by Jimenez-Banzo et al. [*Photochem Photobiol Sci* 2008, 7:1003-1010], using a thermoelectric cooled NIR PMT module (model H10330-45, Hamamatsu, Japan) equipped with a 1100 nm cut-off filter and additional selected narrow-band filters (NB series, NDC Infrared Engineering LTD, Maldon, UK). Data were collected using a computer-mounted PCI-board multi-channel scaler (NanoHarp 250, PicoQuant GmbH, Germany).

Example 1

Sequestration of Imidazoacridinones (IAs) in Cancer Cell Lysosomes and Subsequent Photodestruction of Lysosomes While conceiving the present invention, it was hypothesized, based on the properties and structural similarity of imidazoacridinone (IAs) and acridine orange, that IAs may accumulate within lysosomes, similarly to acridine orange.

In order to explore this hypothesis, the subcellular localization of C-1330, an exemplary, previously disclosed, imidazoacridinone, was compared with that of LysoTracker® Red, an established lysosomal marker. For comparison, the subcellular localization of C-1330 was also compared with that of MitoTracker® Red, an established viable mitochondrial marker. Parental A549 non-small cell lung cancer cells and their ABCG2-overexpressing MDR (multi-drug resistant) subline A549/K1.5 were used. The nuclei were viably counterstained with Hoechst 33342.

As shown in FIG. 2, A549 and A549/K1.5 cells displayed co-localization of the red fluorescence of LysoTracker®-labeled lysosomes with the green fluorescence of C-1330, resulting in an orange fluorescence in the merged photographs. This result indicates that C-1330 is localized to the lysosomes of the cells.

Essentially the same results were obtained with other IAs such as C-1375, C-1379 and C-1311 (data not shown), indicating that localization to lysosomes is a general property of IAs.

As shown in FIG. 3, A549 and A549/K1.5 cells did not display co-localization of the red fluorescence of MitoTracker®-labeled mitochondria with the green fluorescence of C-1330.

This result confirms that C-1330 accumulates in lysosomes and not in mitochondria.

As further shown in FIG. 2, the number of lysosomes stained with either LysoTracker® Red or C-1330 in A549/K1.5 cells was much higher than that observed in parental A549 cells. This result indicates that the multi-drug resistant A549/K1.5 cells comprise considerably more lysosomes than do the A549 cells.

In order to corroborate this finding, the LysoTracker® Red fluorescence per cell was quantified in multiple experiments, EZQuant software.

As shown in FIG. 4, a 6.3-fold increase in the number of lysosomes per A549/K1.5 cell was observed, when compared with A549 cells.

Further corroboration of these findings was shown enzymatically, using β-hexosaminidase activity as an established enzymatic lysosomal marker. Thus, in catalytic activity assays in the presence of a colorimetric substrate of β-hexosaminidase, it was found that MDR A549/K1.5 cells exhibit an enzymatic activity which is about 3-4 folds higher than exhibited in corresponding parental A549 cells.

In order to determine whether the acidic luminal pH of lysosomes is the driving force for the differential, marked compartmentalization of IAs in lysosomes, the pH of lysosomes was increased (i.e., alkalinized) by pre-incubating the cells with ammonium chloride, a weak base lysosomotropic alkalinization agent, or bafilomycin A1, a potent inhibitor of $H^+$-ATPase (vesicular ATPase).

Cells were pre-incubated with 10 mM ammonium chloride for 30 minutes or with 1 μM bafilomycin A1 for 60 minutes, prior to being incubated with 10 μM C-1330 for 30 minutes as described hereinabove. Ammonium chloride and bafilomycin A1 remained present during the incubation with C-1330.

As shown in FIG. 5, ammonium chloride and bafilomycin A1 both completely abolished the lysosomal accumulation of C-1330 in A549 and A549/K1.5 cells.

As further shown therein, ammonium chloride and bafilomycin A1 both induced an exclusive, intense DNA staining by C-1330 in A549 and A549/K1.5 cells.

During the fluorescence microscopy analysis of lysosomal accumulation of C-1330, it was surprisingly observed that immediately upon microscope illumination, lysosomes in both A549 and A549/K1.5 cells began to disappear, appearing as multiple asynchronous flashes.

As shown in FIGS. 6A-6F, illuminated A549 (FIGS. 6A-6C) and A549/K1.5 (FIGS. 6D-6F) cells were characterized by a continuous disappearance of lysosomes and by a parallel gradual increase in nuclear C-1330 fluorescence.

These results indicate that C-1330 causes rupture of lysosomes in the presence of illumination (i.e., photodestruction of lysosomes), resulting in release of C-1330 from the lysosomes, followed by binding of the C-1330 to DNA.

In view of the high fluorescence quantum yield of IAs along with the observed instantaneous lysosomal photodestruction, it was hypothesized that the underlying basis for the rapid rupture of lysosomes and release of C-1330 was the formation of reactive oxygen species (ROS) which lyse the membrane of the lysosomes. In order to test this hypothesis, the effect of ROS scavengers on lysosomal photodestruction was determined.

Monolayers of A549 cells were grown in glass-bottom plates and were washed in growth medium. The medium was then replaced with a special isotonic balanced salt solution lacking or containing either N,N'-dimethylthiourea (DMTU), a potent hydroxyl radical and hydrogen peroxide scavenger, L-histidine, a hydroxyl radical and singlet oxygen radical ($^1O_2$) scavenger, or sodium azide, a singlet oxygen radical scavenger. The salt solution consisted of 10 mM HEPES pH 7.4, 120 mM NaCl, 5 mM KCl, 1 mM $CaCl_2$, 1 mM $MgCl_2$, and 25 mM glucose. After incubation for 1 hour, C-1330 was added to the aforementioned solution buffer for an additional 30 minutes, during which the scavengers remained present, in order to load lysosomes. The cells were then examined by fluorescent imaging as described hereinabove.

Figure 7B:
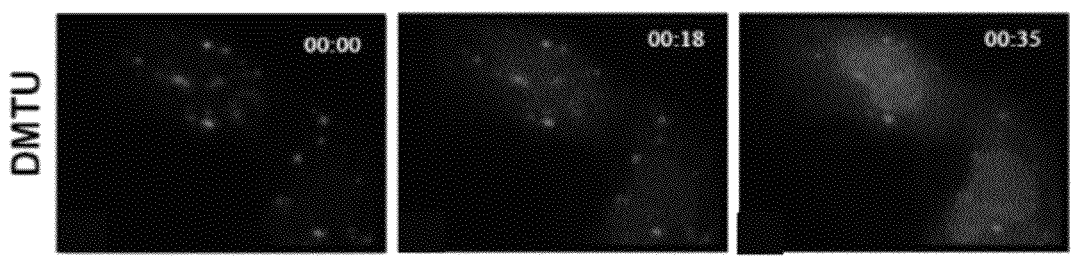
Figure 7C:
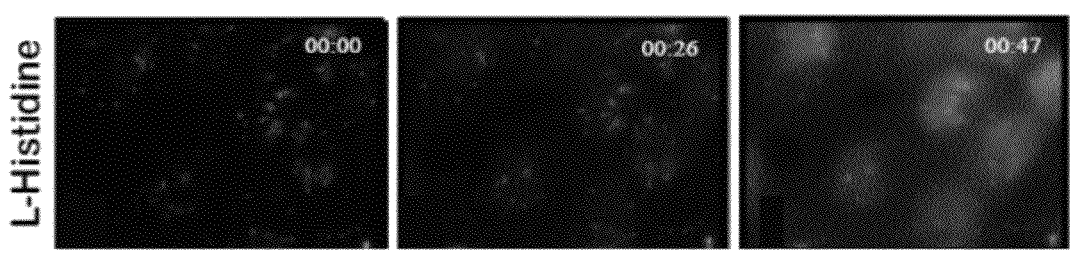
Figure 7D:
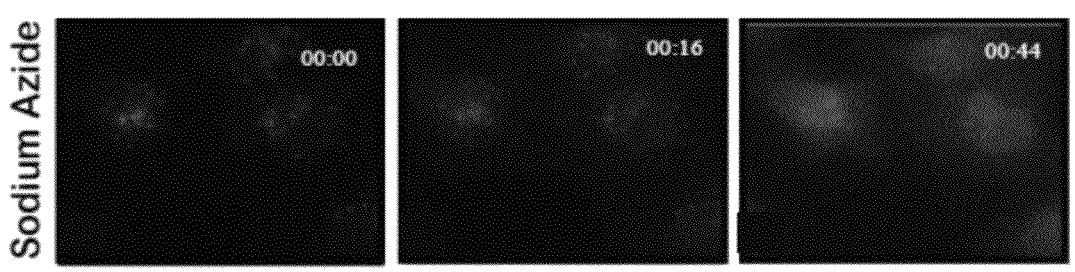

As shown in FIGS. 7A-7D, cells lacking ROS scavengers displayed a typical lysosomal photodestruction upon illumination (FIG. 7A), whereas the ROS scavengers inhibited lysosomal photodestruction (FIGS. 7B-7D).

This antioxidant-dependent inhibition of lysosomal photodestruction was quantified as the time lapse necessary to initiate lysosomal rupture and onset of nuclear staining. Such a quantitative analysis confirmed that the ROS scavengers conferred a markedly prolonged time of protection against lysosomal photodestruction (data not shown).

These results indicate that C-1330-dependent lysosomal photodestruction is mediated by generation of ROS which leads to the rupture of lysosomal membranes.

Example 2

Effect of Lysosome Photodestruction on Imidazoacridinone (IA) Cytotoxicity

The effect of photodestruction of IA-loaded lysosomes on cell viability was investigated in parental A549 and ABCG2-overexpressing A549/K1.5 cells.

Monolayers of A549 and A549/K1.5 cells were pulse-incubated with C-1330 for 30 minutes, washed with drug-free medium, subjected to illumination for 1 minute with a fluorescence microscope, and incubated for 48 additional hours in growth medium. The confluent monolayers were then washed with PBS, fixed with methanol, and stained with crystal violet. The monolayers were then examined by light microscopy.

As shown in FIGS. 8A-8C, in the areas that were illuminated, the cells were completely lysed and eradicated, hence forming pyknotic nuclei-rich blank spaces in the previously confluent monolayers. In contrast, adjacent cells that were not exposed to light retained their intact morphology, and continuous confluent monolayers were observed.

These results indicate that photodestruction of lysosomes considerably enhances the cytotoxicity of C-1330.

As described in Example 1, ABCG2-overexpressing MDR A549/K1.5 cells comprise a markedly increased number of lysosomes per cell. It was therefore hypothesized that MDR cells may be particularly sensitive to the cytotoxic effect mediated by lysosome rupture. To test this hypothesis, the cytotoxic effect of C-1330 was quantitatively determined in A549 and A549/K1.5 cells in the presence or absence of illumination. The cytotoxic effects of C-1375 and C-1379 were also quantitatively determined.

As shown in Table 1, A549/K1.5 cells displayed a 2.5-fold resistance to C-1330 when compared to the parental A549 cells, but photoexcitation of C-1330-loaded cells brought about a 6- and 14-fold decrease in the $IC_{50}$ values of A549 and A549/K1.5 cells, respectively, resulting in identical sensitivity of A549 and A549/K1.5 cell to C-1330 under illumination.

TABLE 1

Effect of exemplary imidazoacridinones (IAs) on survival of A549 and A549/K1.5 cells, with and without illumination

| IA | Cell line | $LD_{50}$ (nM) Control | $LD_{50}$ (nM) Illumination | Fold sensitization | Survival at 3000 nM (%) Control | Survival at 3000 nM (%) Illumination |
|---|---|---|---|---|---|---|
| C-1330 | A549 | 5023 ± 716 | 842 ± 208 | 6 | 72 ± 5 | 43 ± 6 |
| | A549/K1.5 | 12269 ± 1119 | 850 ± 23 | 14 | 87 ± 4 | 28 ± 1 |
| C-1375 | A549 | 3054 ± 260 | 212 ± 29 | 14 | 50 ± 3 | 3 ± 2 |
| | A549/K1.5 | 5264 ± 877 | 541 ± 56 | 10 | 70 ± 5 | 3 ± 0.6 |
| C-1379 | A549 | 6349 ± 867 | 199 ± 31 | 32 | 60 ± 1 | 2 ± 0.3 |
| | A549/K1.5 | 15192 ± 580 | 747 ± 45 | 20 | 82 ± 4 | 7 ± 0.1 |

As shown in FIGS. 9A and 9B, illuminated A549 cells displayed a two drug-target cytotoxicity kill curve with a "bend" occurring near the $IC_{50}$ (FIG. 9A), whereas illuminated A549/K1.5 cells exhibited a smooth cell kill curve with a single drug target (FIG. 9B).

As further shown in Table 1 and in FIGS. 9A and 9B, the presence of 3 μM of C-1330 resulted in a large difference (59%) in the survival of illuminated and non-illuminated MDR A549/K1.5 cells, whereas a significantly smaller difference was obtained with A549 cells (29%).

Similarly, as further shown in Table 1, illumination markedly enhanced the cytotoxic activity of C-1375 and C-1379 in A549 and A549/K1.5 cells by 10-32-fold, in comparison to non-illuminated cells.

These results indicate that the enhancement of cytotoxicity by illumination occurs for a variety of IAs. The cytotoxic impact of IAs under illumination was then determined in ABCB1 (P-gp)-overexpressing MDR non-small cell lung cancer SW1573/2R160 cells, as well as in ABCC1 (MRP1)-overexpressing ovarian carcinoma 2008/MRP1 cell, as well as in their parental, non-resistant, cells.

As shown in Table 2, illumination of C-1375-loaded MDR SW/2R160 and 2008/MRP1 cells resulted in a 13- to 51-fold decrease in the $IC_{50}$ values for C-1375, whereas illumination of their parental cells resulted in a 24- to 36-fold decrease in the $IC_{50}$ values. In the absence of illumination, these MDR cells exhibited $IC_{50}$ values in the range of 3.3-5.5 μM, whereas illumination decreased the $IC_{50}$ values to as low as 90-330 nM.

TABLE 2

Effect of C-1375 on survival of multidrug resistant cancer cells and their non-resistant parental cells, with and without illumination

| Cell line | C-1375 $LD_{50}$ (nM) | | Fold sensitization | Survival at 1000 nM (%) | |
|---|---|---|---|---|---|
| | Control | Illumination | | Control | Illumination |
| SW1573 | 5535 ± 596 | 233 ± 5 | 24 | 68 ± 6 | 11 ± 2 |
| SW1573/2R160 | 4384 ± 125 | 330 ± 56 | 13 | 74 ± 3 | 24 ± 4 |
| 2008 | 3280 ± 345 | 90 ± 9 | 36 | 72 ± 0.8 | 11 ± 4 |
| 2008/MRP1 | 5115 ± 889 | 101 ± 0.1 | 51 | 80 ± 2 | 13 ± 3 |

The $IC_{50}$ values exhibited by MDR cells in the presence of illumination are characteristic of parental cell sensitivity to IAs.

Thus, these results indicate that illumination overcomes the drug resistance of MDR cells.

Example 3

Effect of Chloroquine on Imidazoacridinone (IA) Cytotoxicity

It has been previously shown that chloroquine, an antimalarial and a lysosomotropic agent, increases the number and volume of lysosomes in tumor cells [Fan et al., *Bioorg Med Chem* 2006, 14:3218-3222]. In order to determine whether the cytotoxicity of IAs upon illumination can be modulated by increasing the number of lysosomes in tumor cells, A549 cells were exposed to 20, 50 or 100 μM chloroquine, for 24 or 48 hours.

A549 cells were seeded in 96-well plates at a concentration of 500 cells/well for the 48 hour chloroquine treatment, or at a concentration of 1000 cells/well for the 24 hour chloroquine treatment, in a total volume of 100 μl of medium per well. Following an overnight incubation, chloroquine was then added at the indicated concentrations for 24 or 48 hours. Lysosomes were then stained with LysoTracker® Red, detected by fluorescent imaging as described hereinabove, and quantified using EZQuant software.

As shown in FIGS. 10A-10C and FIG. 11, exposure of A549 cells to 20 μM chloroquine for 24 or 48 hours resulted in a considerable increase in the number and volume of lysosomes, as compared to untreated cells. Quantification using EZ-Quant software revealed an increase of 8.4-fold and 21.7-fold in lysosomal fluorescence after 24 or 48 hours, respectively, as compared to untreated cells.

As further shown in FIG. 11, the increase in the lysosomes following exposure of A549 cells to 20, 50 or 100 μM chloroquine for 24 hours was dose-dependent.

The effect of 20 μM chloroquine on the cytotoxicity of C-1330 towards A549 cells was then determined.

As shown in FIGS. 12A-12C and in Table 3, chloroquine treatment considerably increased the degree to which illumination sensitized cells to C-1330. Whereas illumination increased the cytotoxicity of C-1330 6-fold in the absence of chloroquine treatment, illumination increased the cytotoxicity 23-fold after exposure to chloroquine for 24 hours, and 49-fold after exposure to chloroquine for 48 hours. Similarly, whereas illumination decreased survival at 3 μM C-1330 from 72% to 43% in the absence of chloroquine treatment, illumination decreased cell survival from 79% to 29% after exposure to chloroquine for 24 hours, and from 88% to 9% after exposure to chloroquine for 48 hours.

TABLE 3

Effect of chloroquine concentration and incubation time on C-1330-treated A549, with and without illumination

| Chloroquine | | C-1330 $LD_{50}$ (nM) | | Fold sensitization | Survival at 3000 nM (%) | |
|---|---|---|---|---|---|---|
| Conc. (nM) | Incubation time (hours) | Control | Illumination | | Control | Illumination |
| 20 | 24 | 15222 ± 378 | 648 ± 65 | 23 | 79 ± 5 | 29 ± 07 |
| 50 | 24 | 19609 ± 2454 | 637 ± 174 | 31 | 92 ± 7 | 23 ± 2 |
| 100 | 24 | 15048 ± 2886 | 498 ± 64 | 30 | 90 ± 9 | 19 ± 3 |
| 20 | 48 | 34137 ± 3084 | 700 ± 43 | 49 | 88 ± 8 | 9 ± 3 |

These results indicate that chloroquine may be used to sensitize tumor cells to photodynamic therapy which is mediated by photodestruction of lysosomes.

Example 4

Combination of Imidazoacridinone (IA) and ABCG2 Transport Inhibitor for Inducing Photodestruction of Lysosomes Certain IAs such as C-1311 are recognized by ABCG2 as transport substrates, and are hence efficiently expelled from MDR tumor cells [Bram et al., *Mol Pharmacol* 2009, 75:1149-1159]. Consequently, cell lines with ABCG2 overexpression, such as A549/K1.5, are completely devoid of cellular accumulation of C-1311.

Co-treatment of MDR cells for 2 hours with the ABCG2 transport inhibitor fumitremorgin C (10 μM) and with C-1311 (20 μM) resulted in lysosomal accumulation of C-1311 in the cells, and upon illumination, an intense lysosomal photodestruction occurred (data not shown).

These results indicate that ABCG2 transport inhibitors may enhance the accumulation of certain IAs in lysosomes, and thereby enhance photodestruction of lysosomes.

Example 5

Sequestration of Imidazoacridinones (IAs) and Sunitinib in Endothelial Cell Lysosomes and Subsequent Photodestruction of Lysosomes In order to determine whether imidazoacridinone (IA)-based photodynamic therapy (PDT) may be effective against vascular endothelial cells in addition to cancer cells, lysosomal sequestration of the IAs C-1375 and C-1379 and subsequent photodestruction of lysosomes were investigated in vascular endothelial cells in vitro.

In addition, lysosomal sequestration and subsequent photodestruction of lysosomes of sunitinib (an anti-angiogenetic chemotherapeutic agent), an exemplary chemotherapeutic agent which is a chromophoric, hydrophobic weak base, and which otherwise exhibits little structural similarity to imidazoacridinones, were also investigated.

Freshly-isolated human umbilical vein endothelial cells (HUVEC), RF24 immortalized HUVEC cells, and human dermis derived endothelial cells (HMEC) were obtained and grown in vitro as described in the Materials and Methods section hereinabove. The cells were then seeded at $10^4$ cells/well in a 24-well tissue culture plate. Twenty four hours after seeding, the cells were incubated for 1 hour with 10 or 1 μM of either C-1375, C-1379 or sunitinib. After this incubation, the cells in the 24-well plates were evaluated by fluorescence microscopy. For excitation and detection of imidazoacridinones (IAs) or sunitinib, the microscope was equipped with a filter set (Nikon) characterized by excitation wavelengths of 420±20 nm and emission wavelengths of >470 nm.

As shown in FIGS. 13A and 13B, following incubation of HUVEC cells with 1 μM C-1375, the C-1375 was sequestered in lysosomes and absent from the nuclei (FIG. 13A), whereas upon subsequent exposure to illumination for 1 minute, many lysosomes were destroyed and C-1375 accumulated in the nuclei.

Figure 14A:
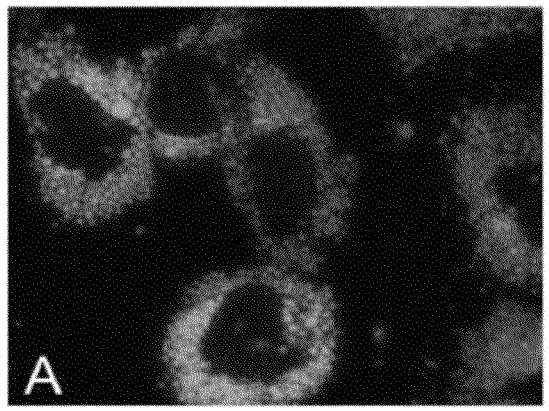
Figure 14B:
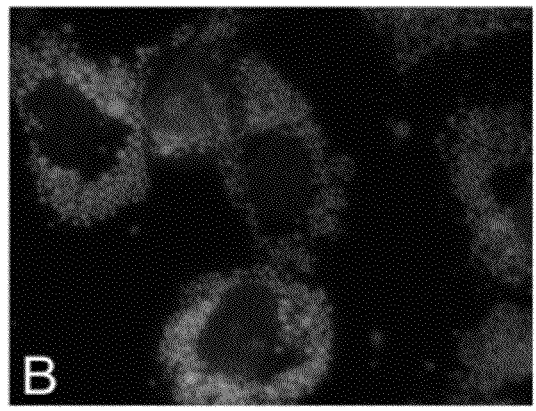
Figure 14C:
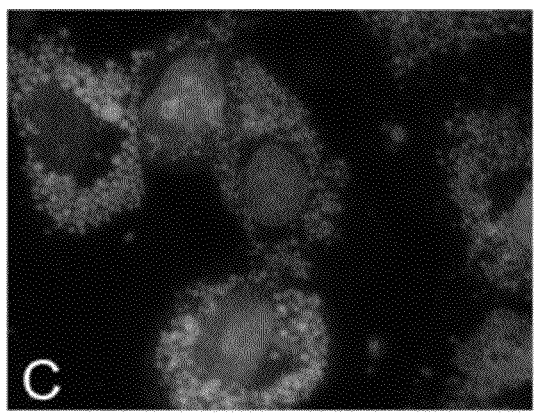
Figure 14D:
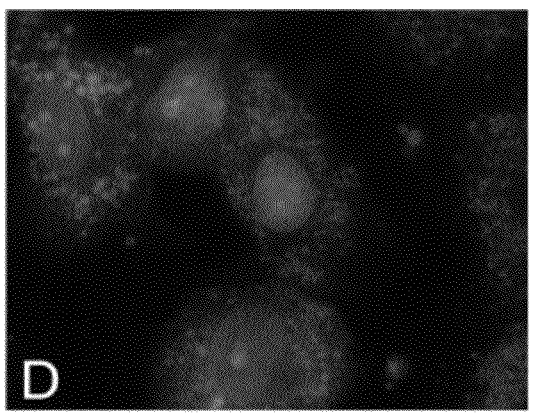

Similarly, as shown in FIGS. 14A-14D, following incubation of HUVEC cells with 1 μM C-1375, the C-1375 was sequestered in lysosomes and absent from the nuclei (FIG. 14A), whereas upon subsequent exposure to illumination, destruction of lysosomes was observed (FIG. 14B), followed by accumulation of C-1375 in the nuclei (FIGS. 14C and 14D). After approximately 2 minutes of illumination, most of the lysosomes had disappeared (FIG. 14D).

As shown in FIGS. 15A and 15B, lysosome destruction and accumulation of C-1375 in the nuclei also occurred upon illumination of HMEC cells, following incubation with 1 μM C-1375.

As shown in FIG. 16, C-1375 was sequestered in lysosomes of RF24 cells and absent from the nuclei, following incubation with 1 μM C-1375.

Similar results were obtained for C-1379 in freshly isolated HUVEC, RF24 and HMEC cells (not shown).

As shown in FIG. 17, sunitinib was sequestered in lysosomes and absent from the nuclei, following incubation with 1 μM sunitinib.

The level of sunitinib fluorescence in lysosomes was slightly lower than that obtained with IAs, and the subsequent photodestruction of lysosomes (not shown) was observed to be slower as well.

Similar results were obtained for sunitinib when incubated with RF24 or HMEC endothelial cells (not shown).

These results indicate that both IAs and sunitinib are sequestered in the lysosomes of endothelial cells and that subsequent illumination results in destruction of the lysosomes.

The above results suggest that photoactivation of a variety of chemotherapeutic agents can be used to kill cells, including vascular cells. Thus, photoactivation of chemotherapeutic agents may be used to inhibit and even reverse tumor growth by an anti-angiogenetic effect of killing vascular cells surrounding a tumor and/or by killing tumor cells.

Example 6

Photoinduced Cytotoxicity of Imidazoacridinones (IAs) in Vascular Cells

As described in Example 5, imidazoacridinones (IAs) can facilitate photodestruction of lysosomes in endothelial cells, suggesting that photodynamic therapy (PDT) utilizing IAs may be used to destroy vascular cells, thereby providing an anti-angiogenetic mechanism of treatment.

In order to further investigate whether imidazoacridinone-based PDT may be effective against vascular cells, the cytotoxicities of the IAs C-1375 and C-1379 under illumination were studied in a chicken chorioallantoic membrane (CAM) model, as described in the Materials and Methods section hereinabove.

The absorption, emission and excitation spectra of C-1375 and C-1379 were determined in an aqueous solution with 0.9% NaCl, as described in the Materials and Methods section. The two IAs exhibited similar spectroscopic characteristics, with absorbance in a range 340-500 nm with molar extinction coefficients on an order of $10^4$ $cm^{-1}$ $M^{-1}$. The wavelengths of peak absorption, emission and excitation are presented in Table 4 below. The normalized fluorescent spectra (excitation and emission spectra) of C-1379 are shown in FIG. 18. As shown in FIG. 18, the emission consisted of a single broad band, and the shape of the excitation band was similar to that of the absorption band.

TABLE 4

| Spectroscopic characteristics of C-1375 and C-1379 | | | |
|---|---|---|---|
| Compound | Peak absorption (nm) | Peak emission (nm) | Peak excitation (nm) |
| C-1375 | 444 | 553 | 449 |
| C-1379 | 443 | 554 | 447 |

Based on the above results, filtered light with a wavelength of 420±20 nm was used for illumination. The fluorescence of the IAs was observed by detecting wavelengths above 470 nm.

Photodynamic therapy (PDT) was performed at embryo development day (EDD) 11, at which stage the CAM is fully developed and contains a vessel network with a regular capillary plexus. The imidazoacridinones were intravenously injected into the main vessel of the CAM through a 33-gauge needle fitted to a 100 μl syringe (Hamilton), at a concentration of 1 mg/ml and a volume of 100 μl, which corresponds to a dose of 100 μg, or approximately 10 mg/kg embryo body weight.

As shown in FIGS. 19A and 19B, fluorescence of the IAs was observed in the vasculature of the CAMs prior to PDT.

One minute after injection, a region of the CAM which contained vessels of diameters in a range of 5 to 70 μm was illuminated (420±20 nm) at a light dose of 20 $J/cm^2$ and an irradiance of 270 mid/cm². The illuminated area was 0.02 cm², as delimited by an optical diaphragm.

As shown in FIG. 19C, IA fluorescence was observed in the vasculature of the CAMs immediately after PDT, and was particularly intense in the endothelial lining.

This result indicates that IA is present primarily in the vasculature during PDT treatment, and apparently undergoes uptake into lining endothelial cells during and/or after treatment, which may enhance vascular damage.

24 hours after illumination, the illuminated area was visualized by fluorescein isothiocyanate (FITC)-dextran fluorescence angiography, as well as by observing IA fluorescence, as described hereinabove.

As shown in FIGS. 20A-21B, illumination in the presence of either C-1379 (FIGS. 20A and 21A) or C-1375 (FIGS. 20B and 21B) resulted in vaso-occlusion within the illuminated area 24 hours after treatment, as was observed by both FITC-dextran (FIGS. 20A and 20B) and IA (FIGS. 21A and 21B) fluorescence angiography. The illuminated areas were largely free of fluorescence, indicating an avascular zone.

The effect of lower doses of IA was also investigated. The above experiment was also performed with a C-1379 dose of 1 µg/embryo instead of 100 µg/embryo.

As shown in FIGS. 22A and 22B, illumination in the presence of the low dose of C-1379 resulted in massive occlusion of the capillary network, although larger blood vessels remained perfused, as was observed by FITC-dextran angiography.

These results indicate that photodynamic therapy using imidazoacridinones can be effective at destroying vasculature in addition to tumor cells, in a dose-dependent manner.

Example 7

Photoinduced Cytotoxicity of Sunitinib in Vascular Cells

As described in Example 5, sunitinib can facilitate photodestruction of lysosomes in endothelial cells, suggesting that photodynamic therapy (PDT) utilizing sunitinib may be used to destroy cells, thereby providing, for example, an anti-angiogenetic treatment mechanism.

In order to further investigate whether sunitinib is suitable for photodynamic therapy (PDT), the cytotoxicity of sunitinib under illumination was studied in a chicken chorioallantoic membrane (CAM) model, as described in the Materials and Methods section hereinabove.

The absorption, emission and excitation spectra of sunitinib were determined in an aqueous solution with 0.9% NaCl, as described in the Materials and Methods section. Sunitinib absorbs light at wavelengths of 340-480 nm, with the absorption peak being at 429 nm. When excited at 429 nm, sunitinib exhibited strong fluorescence as a single broad emission band with an emission peak at 510 nm. Peak excitation was obtained at a wavelength of 407 nm.

Based on the above results, filtered light with a wavelength of 420±20 nm was used for illumination, and sunitinib fluorescence was observed by detecting wavelengths above 470 nm.

Photodynamic therapy (PDT) was performed at embryo development day (EDD) 11, using the treatment protocols summarized in Table 5 below.

TABLE 5

Treatment protocols for photodynamic therapy with sunitinib

| Protocol No. | Administration route | Sunitinib dose µg/per embryo | Sunitinib dose mg/kg body weight | Drug-light interval | Irradiance (mW/cm²) | Light dose (J/cm²) |
|---|---|---|---|---|---|---|
| 1 | intravenous | 0.002 | 0.0002 | 1 minute | 70 | 34 |
| 2 | intravenous | 12 | 1.2 | 1 minute | 270 | 130 |
| 3 | intravenous | 200 | 20 | 3 hours | 270 | 130 |
| 4 | topical | 40 | 4 | 3 hours | 270 | 130 |

Sunitinib was administered intravenously (in protocols 1-3) in a volume of 20 µl into the main vessel of the CAM through a 33-gauge needle fitted to a 100 µl syringe (Hamilton).

Sunitinib was administered topically (in protocol 4) by depositing 20 µl of sunitinib solution into a polyethylene ring (5 mm in diameter) placed on the CAM. The solution was removed 3 hours later, shortly before illumination of the treated area.

One minute or 3 hours after injection, a region of the CAM was illuminated (420±20 nm) as indicated in Table 5. The illuminated area was 0.02 cm², as delimited by an optical diaphragm. The fluorescence of sunitinib was visible in the vasculature of the CAMs prior to PDT.

24 hours after illumination, the illuminated area was visualized by fluorescein isothiocyanate (FITC)-dextran fluorescence angiography, as well as by observing sunitinib fluorescence, as described hereinabove.

As shown in FIGS. 23A-23D, illumination following intravenous administration of 0.0002 mg/kg sunitinib (FIGS. 23A and 23B) resulted in vaso-occlusion within the illuminated area 24 hours after treatment, whereas illumination in the absence of sunitinib (FIGS. 23C and 23D) did not, as was observed by FITC-dextran (FIGS. 23B and 23D) fluorescence angiography. The area illuminated in the presence of sunitinib (FIG. 23B) included regions free of fluorescence, indicating capillary bed occlusion, with large vessels remaining patent.

Similarly, as shown in FIGS. 24A-24E, illumination following intravenous administration of 1.2 mg/kg sunitinib (FIGS. 24A-24C) resulted in vaso-occlusion within the illuminated area immediately after treatment (FIG. 24B), and was particularly pronounced 24 hours after treatment (FIG. 24C), whereas illumination in the absence of sunitinib (FIGS. 24D and 24E) did not result in vaso-occlusion, as was observed by FITC-dextran (FIGS. 24C and 24E) and sunitinib (FIGS. 24A and 24B) fluorescence angiography. The areas illuminated in the presence of sunitinib (FIGS. 24B and 24C) were free of fluorescence, except in large vessels, indicating complete capillary bed occlusion, with large vessels remaining patent.

As shown in FIGS. 25A-25C, illumination following intravenous administration of 20 mg/kg sunitinib resulted in vaso-occlusion within the illuminated area 24 hours after treatment, as was observed by FITC-dextran (FIG. 25B) and sunitinib (FIG. 25C) fluorescence angiography. Avascular zones were observed as black areas. Occluded vessels were observed as black when visualized by FITC-dextran fluorescence angiography (FIG. 25B), but were extensively stained by bright spots when visualized by sunitinib fluorescence angiography (FIG. 25C). Prior to illumination, the membrane exhibited strong autofluorescence, such that the blood vessels appeared as dark lines against a light background (FIG. 25A).

These results suggest that PDT with 20 mg/kg sunitinib can occlude whole vessels as a result of sunitinib uptake into the vascular cells.

As is further shown in FIGS. 23A-25C, sunitinib fluorescence is visible within the vasculature when administered intravenously.

In contrast, as shown in FIGS. 26A and 26B, sunitinib fluorescence is visible exclusively outside the vasculature when administered topically.

As shown in FIGS. 26A and 26B, illumination following topical of 4 mg/kg sunitinib resulted in vaso-occlusion within the illuminated area 24 hours after treatment, as was observed by FITC-dextran (FIG. 26B) fluorescence angiography. Avascular zones were observed as black areas in FITC-dextran fluorescence angiography.

The above results indicate that sunitinib can be effective for photodynamic therapy, following intravenous or topical administration.

Example 8

Sequestration of Doxorubicin in Lysosomes and Subsequent Photodestruction of Lysosomes Doxorubicin is an additional example of a chemotherapeutic agent which is a chromophore and a hydrophobic weak base. Doxorubucin is an anthracycline drug, and exhibits little structural similarity to either imidazoacridinones or sunitinib. It was therefore investigated whether doxorubicin is sequestered in lysosomes and whether subsequent illumination would lead to photodestruction of lysosomes.

A549/K1.5 cells were incubated with 10 µM doxorubicin for 30 minutes, and then observed and illuminated (at 470 nm) by live cell fluorescent imaging as described in the Materials and Methods section. Upon illumination, the cells were photographed every second, in order to observe changes in the cells over time.

As shown in FIGS. 27A-27C, doxorubicin accumulates in lysosomes (FIG. 27A), and upon illumination, the lysosomes rupture and the doxorubicin accumulates in the cell nuclei (FIGS. 27B and 27C). As shown in FIG. 27C, after 20 seconds of illumination, nearly all of the lysosomes had ruptured, and intense nuclear staining by doxorubicin was observed, indicating binding of DNA by doxorubicin.

These results indicate that photodynamic therapy with doxorubicin induces destruction of lysosomes and subsequent binding of DNA by doxorubicin in the cell nuclei. As doxorubicin is known to exert a chemotherapeutic effect by binding DNA (by intercalation), these results suggest that photodestruction of lysosomes can enhance the effect of doxorubicin by facilitating binding of DNA by doxorubicin.

The above results also suggest that a wide variety of chemotherapeutic agents can be effective for photodynamic therapy associated with lysosomal destruction.

Example 9

Treatment of Tumors by Imidazoacridinone-Based Photodynamic Therapy

The efficacy of PDT following administration of an imidazoacridinone was investigated using tumors transplanted onto a chicken chorioallantoic membrane (CAM).

Human A2780 ovarian carcinoma cells were used to establish tumor xenografts in the CAM. Tumor spheroids were grown by a hanging drop technique, resulting in spheroids with a predefined size. A2780 cells were suspended in medium containing 20% Methocel™ (Sigma-Aldrich, St. Louis, USA), and 50 µl drops ($1 \times 10^6$ cells/drop) were dispensed on the internal part of the lid of a Petri dish. After 24 hours, spheroids were harvested and placed on the CAM at embryonic development day (EDD) 7. Two transplanted human A2780 ovarian carcinoma tumor spheroids, containing $10^6$ cells, were grown on a single CAM, and 300 µM C-1379 was injected intravenously at a concentration of 12 µg per embryo at EDD 11.

Prior to further treatment, both tumors were imaged by imidazoacridinone (C-1379) fluorescence angiography, as described hereinabove. One minute after C-1379 administration, one of the tumors was illuminated at a wavelength of 420 nm (34 J/cm$^2$, 70 mW/cm$^2$). 24 hours later, both tumors were visualized by FITC-dextran angiography, as described hereinabove, and by standard photography. Immediately thereafter, a second round of C-1379 intravenous administration and PDT (on one of the tumors) was performed as previously. The CAM was then incubated for two more days. The tumors were then visualized again by FITC-dextran angiography and by standard photography (72 hours after the first treatment and 48 hours after the second treatment).

As shown in FIGS. 28A-28F and 29A-29D, photodynamic therapy using C-1379 (FIGS. 28A-28C and 29A-29B) resulted in vaso-occlusion and destruction of tumor vasculature, and subsequent inhibition of tumor growth, in comparison with C-1379 treatment without photodynamic therapy (FIGS. 28D-28F and 29C-29D). The illuminated tumors exhibited signs off blood clotting and necrosis, particularly in the central part of the tumor. As further shown in FIGS. 28C and 29B, considerable leakage of FITC-dextran from the vasculature occurred after PDT treatment, indicating extensive vascular dysfunction.

These results indicate that PDT using imidazoacridinones is effective at killing tumors.

Example 10

Effect of Lysosome Photodestruction on Cytoskeletal Structure

In order to further evaluate the effects of lysosomal photodestruction, and the mechanism by which lysosomal photodestruction leads to cell death, the cytoskeletal structure of cells was detected before or after lysosomal photodestruction by labeling F-actin with a Texas Red-phalloidin conjugate according to well established procedures. Phalloidin is a bicyclic peptide belonging to a family of toxins isolated from *Amanita phalloides* and is widely used in fluorescence imaging applications to selectively label F-actin. Lysosomal photodestruction was effected by incubation of cells with C-1330 followed by illumination, as described in the Materials and Methods section hereinabove.

As shown in FIGS. 30A and 30B, cells which were incubated with C-1330 and then illuminated exhibited considerable damage, with the cells being devoid of cytoplasmic content and actin cytoskeleton, and with a deformed residual cytoskeletal structure remaining only at the cell perimeter (FIG. 30B), whereas cells incubated with C-1330 without illumination retained a normal actin cytoskeleton (FIG. 30A).

These results further confirm that lysosomal photodestruction result in severe damage to cells, particularly in the inner portions of the cell.

Example 11

ROS Production by Imidazoacridinone Photosensitization

It was hypothesized that photo-induced lysosome destruction described herein is a result of ROS production by photosensitization, which may cause lysis of lysosomal membranes. In order to test this hypothesis, ROS production upon illumination of imidizoacridinones was measured.

Generation of the ROS singlet oxygen was determined by direct detection of singlet oxygen luminescence at a wavelength of approximately 1270 nm, as described hereinabove. C-1375 and C-1379 (in acetonitrile and DMSO solutions) were excited by pulsed excitation with 355 nm laser radiation, and singlet oxygen generation was measured.

As shown in FIG. 31, photoexcitation of C-1375 and C-1379 resulted in measurable luminescence which was linearly correlated to the intensity of irradiation, indicating singlet oxygen generation by photosensitization. For comparison, luminescence following irradiation of Rose Bengal and riboflavin is also shown.

The luminescence exhibited a lifetime of the order of 3 microseconds in samples that were saturated with either oxygen or air (data not shown). The lifetime of the luminescence was consistent with the reported lifetime of singlet oxygen in such solvents [Korinek et al. *J Fluoresc* 2004, 14:71-74].

Generation of superoxide was determined using EPR (electron spin resonance) spectroscopy with DMPO as a spin trap, as described hereinabove. Generation of superoxide was measured for solutions of both C-1375 and C-1379 in a mixture of DMSO and $H_2O$ (9:1). 1 mM NADH was added, which considerably enhanced the EPR signal of the DMPO-superoxide spin adduct (data not shown).

As shown in FIG. 32, an EPR signal of the DMPO-superoxide spin adduct (DMPO—OOH) increased overtime upon irradiation of C-1375 or C-1379 in the presence of 1 mM NADH. The EPR signal was fully consistent with the spin trapping of superoxide anion by DMPO. For comparison, spin adduct formation upon irradiation of riboflavin with EDTA is also shown.

These results indicate that imidazoacridinones generate ROS such as singlet oxygen and superoxide radical anion upon photoexcitation, particularly in the presence of an electron donor such as NADH, and suggest that lysosomal photodestruction is mediated by the generation of ROS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of enhancing a cytotoxicity of an imidazoacridinone chemotherapeutic agent towards cells in a region that comprises a tumor in a body of a subject in need thereof, the method comprising administering to the subject said imidazoacridinone chemotherapeutic agent and illuminating said region, wherein said imidazoacridinone chemotherapeutic agent is a hydrophobic weak base and acts as a photosensitizer when exposed to illumination at a wavelength in a range of from 400 to 800 nm, wherein said imidazoacridinone chemotherapeutic agent is selected from the group consisting of C-1330, C-1375, C-1379 and C-1311 and wherein said imidazoacridinone chemotherapeutic agent and a wavelength of said illumination are selected such that said chemotherapeutic agent acts as a therapeutically effective photosensitizer when exposed to said illumination.

2. The method of claim 1, wherein said imidazoacridinone chemotherapeutic agent and said illumination are characterized in that an $IC_{50}$ value of said chemotherapeutic agent when exposed to said illumination is 10% or less of an $IC_{50}$ value of said chemotherapeutic agent in the dark, said $IC_{50}$ values being determined by an XTT cell viability assay.

3. The method of claim 1, wherein said imidazoacridinone chemotherapeutic agent is characterized by a pKa in a range of from 5 to 12, said pKa representing a transition between a neutrally charged state and a positively charged state.

4. The method of claim 1, wherein a neutrally charged state of said imidazoacridinone chemotherapeutic agent is characterized by a logy value of at least 0.5.

5. The method of claim 1, wherein said imidazoacridinone chemotherapeutic agent is administered at a dosage which is 20% or less than a cytotoxic dosage of said imidazoacridinone chemotherapeutic agent.

6. The method of claim 1, wherein said subject is afflicted by a proliferative disease or disorder selected from the group consisting of cancer and hyperplasia.

7. The method of claim 6, wherein said cancer is a multi-drug resistant cancer.

8. The method of claim 1, wherein said cells are selected from the group consisting of lung cancer calls, ovarian cancer cells and vascular endothelial cells.

9. The method of claim 6, wherein said cancer is selected from the group consisting of lung cancer and ovarian cancer.

* * * * *